US009739993B2

(12) United States Patent
Sirat et al.

(10) Patent No.: US 9,739,993 B2
(45) Date of Patent: *Aug. 22, 2017

(54) OPTICAL MEASUREMENT METHOD AND DEVICE

(71) Applicant: Bioaxial SAS, Paris (FR)

(72) Inventors: Gabriel Y. Sirat, Paris (FR); Louis Philippe Braitbart, Paris (FR)

(73) Assignee: Bioaxial SAS (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/391,828

(22) PCT Filed: Apr. 11, 2013

(86) PCT No.: PCT/FR2013/000098
§ 371 (c)(1),
(2) Date: Oct. 10, 2014

(87) PCT Pub. No.: WO2013/153294
PCT Pub. Date: Oct. 17, 2013

(65) Prior Publication Data
US 2015/0212308 A1    Jul. 30, 2015

(30) Foreign Application Priority Data

Apr. 13, 2012 (FR) ..................................... 12 01094
Apr. 13, 2012 (FR) ..................................... 12 01095

(51) Int. Cl.
G02B 21/16    (2006.01)
G02B 21/00    (2006.01)
(Continued)

(52) U.S. Cl.
CPC ......... G02B 21/16 (2013.01); G01N 21/6458 (2013.01); G01N 21/6486 (2013.01);
(Continued)

(58) Field of Classification Search
CPC .................................................. G02B 21/16
See application file for complete search history.

(56) References Cited

U.S. PATENT DOCUMENTS 7,324,273 B2    1/2008  Gweon et al. ................ 359/386
7,541,600 B2    6/2009  Neuhauser et al. ....... 250/491.1
(Continued)

FOREIGN PATENT DOCUMENTS

DE    20 2009 007 250    12/2009
WO    WO 2009/066253    5/2009
(Continued)

OTHER PUBLICATIONS

Abdolvand et al., "Conical refraction Nd:KGd(WO$_4$)$_2$ laser," *Opt. Express*, vol. 18, No. 3, pp. 2753-2759 (Feb. 2010).
(Continued)

*Primary Examiner* — David Porta
*Assistant Examiner* — Hugh H Maupin
(74) *Attorney, Agent, or Firm* — Sunstein Kann Murphy & Timbers LLP

(57) ABSTRACT

The invention relates to an optical measurement method and to an optical measurement device for determining the spatial or spatiotemporal distribution of a sample, the sample comprising at least one retransmission source, said at least one retransmission source retransmitting light depending on the projected light, according to a predetermined law, onto the sample, the method comprising: the projection onto the sample of at least two compact light distributions belonging to different topological families, which propagate along the same optical path, the detection of the light retransmitted by said at least one retransmission source of the sample; the generation of at least one optical image from the detected light; and the algorithmic analysis of the optical images for obtaining location data on said at least one retransmission source.

8 Claims, 13 Drawing Sheets

(51) Int. Cl.
*G01N 21/64* (2006.01)
*G02B 21/36* (2006.01)
(52) U.S. Cl.
CPC ..... *G02B 21/0072* (2013.01); *G02B 21/0076* (2013.01); *G02B 21/361* (2013.01); *G01N 2201/06113* (2013.01); *G01N 2201/12* (2013.01)

(56) References Cited

U.S. PATENT DOCUMENTS

| | | | |
|---|---|---|---|
| 8,514,685 B2 | 8/2013 | Sirat | 369/112.01 |
| 8,542,712 B2 | 9/2013 | Rafailov et al. | 372/66 |
| 2002/0141052 A1 | 10/2002 | Iketaki | 359/386 |
| 2003/0137645 A1 | 7/2003 | Fluckiger | 356/4.01 |
| 2003/0210405 A1 | 11/2003 | Feldman | 356/511 |
| 2007/0070496 A1 | 3/2007 | Gweon et al. | 359/386 |
| 2008/0068588 A1 | 3/2008 | Hess et al. | 356/36 |
| 2009/0168613 A1 | 7/2009 | Sirat | 369/18 |
| 2012/0104279 A1* | 5/2012 | Reuss et al. | 250/458.1 |
| 2013/0176574 A1* | 7/2013 | Sirat | 356/496 |

FOREIGN PATENT DOCUMENTS

| | | |
|---|---|---|
| WO | WO 2010/133678 | 11/2010 |
| WO | WO 2011/086519 | 7/2011 |

OTHER PUBLICATIONS

Berry et al., "Conical diffraction: observations and theory," *Proc. R. Soc. A*, vol. 462, pp. 1629-1642 (Feb. 2006).
Berry, "Conical diffraction from an N-crystal cascade," *J. Opt.*, vol. 12, No. 8, pp. 1-8 (2010).
Boruah, "Lateral resolution enhancement in confocal microscopy by vectorial aperture engineering," *Appl. Optics*, vol. 49, No. 4, pp. 701-707 (Feb. 2010).
Haeberlé et al., "Saturated structured confocal microscopy with theoretically unlimited resolution," *Opt. Comm.*, vol. 282, pp. 3657-3664 (2009).
Hell, "Far-Field Optical Nanoscopy," *Science*, vol. 316, pp. 1153-1158 (May 2007).
Lunney et al., "The ins and outs of conical refraction," *Europhysics News*, vol. 37, No. 3, pp. 26-29 (2006).
Peet, "Biaxial crystal as a versatile mode converter," *J. Opt.*, vol. 12, pp. 1-4 (2010).
Phelan et al., "Conical diffraction and Bessel beam formation with a high optical quality biaxial crystal," *Opt. Exp.*, vol. 17, No. 15, pp. 12891-12899 (Jul. 2009).
Vlokh et al., "Appearance of Optical Vortex at Conical Refraction. Examples of $NaNO_2$ and $YFeO_3$ Crystals," *Ukr. J. Phys. Opt.*, vol. 4, No. 2, p. 90-93 (Jan. 2003).
Züchner, et al., "Light Microscopy with Doughnut Modes: A Concept to Detect, Characterize, and Manipulate Individual Nanoobjects," *Angew. Chem. Int. Ed.*, vol. 50, pp. 5274-5293 (2011).

* cited by examiner

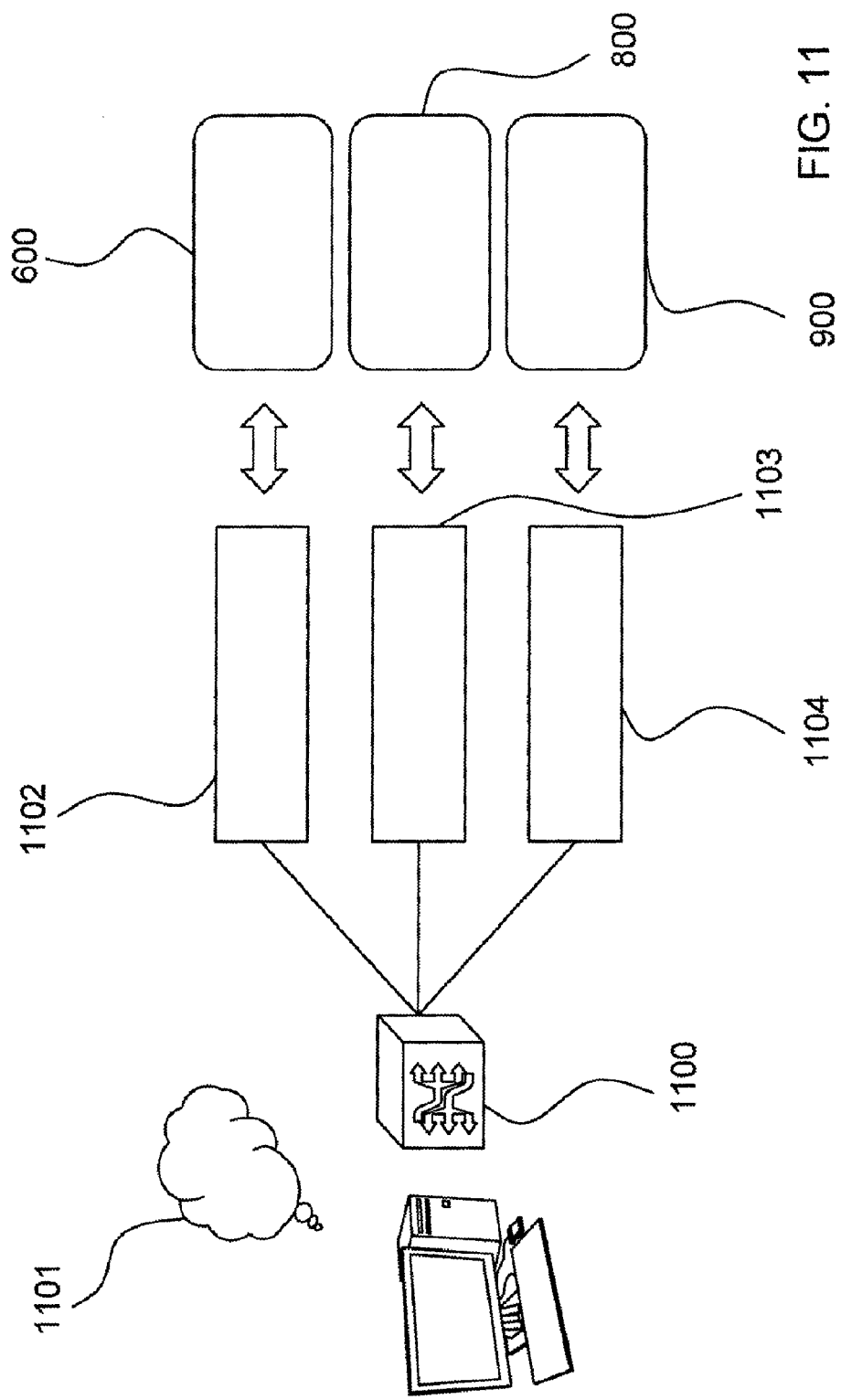

OPTICAL MEASUREMENT METHOD AND DEVICE

The present invention relates to an optical measuring method and device. It applies to all fields of imaging, in particular, though not limited to, the field of Microscopy, including but not limited to the fields of Biology, Medicine, Pharmacy, Semiconductors, materials study, Metrology, control, measurement and observation and to all processes for acquisition of information from optical observations, in the macroscopic or microscopic field.

An optical microscope is an optical instrument generally used to view, analyse or measure objects too small for the naked eye.

We use the term biological to describe any biological entity in Life Science, regardless of its origin, human, animal or plant and the purpose of his observation, research, diagnosis or treatment. This term includes the medical uses of the technique described. Microscopy is used in the field of biology, for example, to observe, study and measure biological entities (objects) and their dynamics.

By extension, the term artificial Vision will be used to describe all measuring applications, Metrology or observation of objects or elements produced or constructed or made by a human being or machine, for example, to observe, study and measure Semiconductors or to characterise materials.

The usual definitions are used for: optical diffraction limit, Rayleigh criterion, Airy disk and its radius and diameter. We use in the context of the invention, the terms of superresolution, superresolved, superresolution imaging and super-resolution microscopy to describe optical data acquisition, optical imaging, microscopy and artificial vision at a resolution higher than the optical diffraction limit. The usual definitions are used for fluorescence and for fluorophores.

Referring now to FIG. 1, which shows an illustration of the paradigm of Microscopy, 100.

Optical microscopes including illumination, by a light source, not shown, using a microscope, 10, of a biological or non-biological sample, 11, and the time-dependent measurement, using either visual observation or a detection module 12, of the light emitted, reemitted, diffused or reflected or transmitted by the sample. In Biology, the sample comprises a single—or a plurality—of different biological entities, 13 and 14, positioned at different positions. Examples of such objects are, among others, a cell, a virus, a protein and a DNA fragment. In artificial industrial vision the sample can be, for example, a semi-conductor element.

Microscopy is segmented into different modalities having different characteristics and purposes. Many descriptions of the different modalities, their characteristics and their advantages exist extensively in the literature and are found for example on the company web sites of Zeiss [1], Leica, Nikon, [2] or Olympus.

Microscopy applications can be structured in many different ways: one of these is distinguishing the modalities of Microscopy for displaying minuscule point sources of those allotted to measure continuous objects.

The case of minuscule point sources is a priori much simpler. The object consists of a small number of light points; the latter can be described by a small number of parameters—the descriptors defined hereinbelow—greatly simplifying the physical problem and the algorithmic complexity. The case of a continuous object describes that spatial distribution- or spatio-temporal, if the dynamic is considered—continuous, is different and is also described in this patent application.

Fluorescence microscopy is one of the modalities of microscopy, it has replaced in many applications, the other microscopy techniques. A fluorescence microscope is an optical microscope used to study properties of objects or of organic or inorganic substances by using the phenomena of fluorescence instead of, or in addition to other modalities such as reflection and absorption.

We refer again to FIG. 1, describing this time a fluorescence microscope either used in biology or artificial vision to characterize, for example, materials; in fluorescence microscopy, tiny point sources, 15 to 18, for example fluorophores, based on the physical phenomenon of one photon fluorescence, are fixed at specific positions of predetermined biological objects, 13 and 14; the light emitted by the point sources is observed instead of observing the light emitted by the objects, 13 and 14, themselves.

The sample is illuminated by light of wavelength, or specific wavelengths, which is absorbed by the point sources, thereby inducing the emission of light at different, higher, wavelengths. During the collection of the light emitted by fluorescence, the illumination light is separated from the emitted fluorescence, which is lower, by the use of a spectral emission filter.

Fluorescence Microscopy studies the light emitted by small point sources, fluorophores. However, when the density of fluorophores is high, fluorophores are no longer analysed individually but treated as a continuous object.

It is important to note, from this stage, that the same system enables observation of continuous objects, and is not limited to the observation of point sources.

Fluorophores have become an important tool for the visualization of biological objects. The activity and the biological information including details above the limit of resolution of 200 nm are systematically viewed and measured using fluorescence microscopy. This resolution limit is derived from the Rayleigh criterion, which in the best case, reaches 200 nm in systems designed specifically. For a long time, until the emergence of superresolution techniques described below, it was recognized that optical techniques, including fluorescence microscopy, are unable to visualize details smaller than the Rayleigh criterion, which is about 200 nm.

However, other fundamental biological activities also occur at scales smaller than 200 nm in biological samples. At this level of spatial resolution, important phenomena can be observed: the biological processes at the scale of intracellular, cell information transfer, the folding and unfolding of the proteins and changes in the DNA and RNA. For example, the measurement of this intracellular information opens new avenues for understanding biological activity, and leads to progress in understanding and monitoring of research and medical diagnostics.

The main implementations of fluorescence microscopy, as described in detail in the literature, are the confocal microscope, often used in a scanning configuration or spinning disc microscope, and the wide-field imaging microscope.

Referring now to FIG. 2 which is a simplified representation of a confocal fluorescence microscope of the prior art 200.

A confocal fluorescence microscope, FIG. 2 is an optical instrument. Its main hardware components are shown in FIG. 2. They include:

a light source, 20,
an optomechanical frame not shown
a cube filter, 21,
a microscope objective 22, and,
a detector assembly, 23,
a processing unit, not shown.

The light source 20, which may be an arc lamp or a laser, creates light energy necessary for fluorescence.

The Optomechanical frame, not shown, is the support of all the optical components and auxiliary optics and includes alignment capacities. It also includes optical elements, not shown, capable of shaping the beam to allow its focus point of a minimum size by means of the microscope objective.

It can also comprise, in a confocal scanning fluorescence, a spatial or angular scanning mechanism, not shown, to change the position of the point source with respect to the object to be measured.

The scanning mechanism can alternatively:

mechanically translate the object, for example by using a translation plate, optically scan the beam on the object, for example using a set of galvanometric mirrors or acousto-optical translators, or use any combination of these translation means, mechanical or optical.

In a confocal scanning fluorescence, the information is collected point by point, using the scanning mechanism.

It can also comprise, in a rotating disk type confocal fluorescence, a rotating disc having a plurality of pinholes, allowing the simultaneous projection of a plurality of points. In a confocal fluorescence rotating disk, a set of points, corresponding to the pinhole is acquired at any time and the rotation of the disk allows to scan the entire surface of the sample for a given longitudinal position.

The cube of filters, 21, channels the different optical signals and avoids contamination of the fluorescence signal by the excitation light. The cube is composed of filters: excitation filter, 210 dichroic mirror, 211, and emission filter 212. The filters and the dichroic mirror are selected according to the wavelength of excitation and emission spectral characteristics of the fluorophore.

The microscope objective 22 focuses the light created by the source in the focal plane of the lens 24, a light distribution pattern of small size, and the optimum light distribution consisting of the Airy disk. The microscope objective 22, also collects back fluorescent light emitted by the fluorophores.

For a confocal scanning fluorescence the system can be descanned, that is to say, the return light can pass through the scanning mechanism to compensate for the translation due to scanning A detector lens, 25, creates, in the image plane of the detector 26, a magnified image of the focal plane of the lens 24.

A confocal hole, 27, is theoretically placed in the image plane of the detector 26.

In most practical systems, the confocal hole, 27, is placed in an intermediate imaging plane, not shown, and reimaged onto the image plane of the detector 26.

The assembly of the detector, 23, detects the fluorescent intensity in the overall illuminated volume, and converts it into digital signal. For a confocal scanning microscope, the detector including a detector of a single element, such as a PMT or SPAD. For a confocal microscope using a rotary disc, the detector including a matrix of detector elements, such as a CCD, an EMCCD, a CMOS or a matrix of SPAD.

All components mounted from the light source to the dichroic filter are the illumination path, 201. The detection channel, 202, represents all the components mounted from the dichroic filter to the assembly of the detector.

The elementary optical process of a confocal microscope can be segmented into six steps:

Projecting light on the volume analysed

Fluorescent light emission by fluorophores

Imaging of the fluorophores in the focal plane

Limitation in the focal plane of light analysed by confocal hole

Integration of light analysed by a photoelectric detector

Display of the measured intensity as a pixel value in an image

Fluorescence microscopes are available from several manufacturers, such as Nikon, Zeiss, Leica and Olympus. Fluorescence microscopes can be either standard microscopes suitable for fluorescence or microscopes optimised specifically for fluorescence. Modern microscopes are versatile instruments capable of operating in many different modalities, including, but not limited to, fluorescence modalities, using the same platform and most optomechanical components. Most fluorescence microscopes are developed as an open platform, capable of performing several additional features with minimal modifications. Other fluorescence microscopes are instruments dedicated, adapted for a specific task, such as medical diagnosis or pharmaceuticals.

Superresolution

New optical methods, methods for superresolution are capable of discriminating point sources, below the Rayleigh criterion. These methods are being developed by several companies, laboratories and researchers and some of the instruments using these methods, the superresolution microscopes, are commercially available. Several comparative analysis of superresolution methods have recently been published in the literature, as the articles by Schermelleh et al. [3].

An updated bibliography on the superresolution is on the website of the company Zeiss, [1], and on the website of the company Nikon. [2]

Different existing methods of microscopy and existing microscopes, not incorporating the superresolution, allow microscopic observation up to the optical diffraction limit. This reduces their field of use to a limited set of applications.

New superresolution techniques allow to obtain information beyond the resolution limit. The main problem of all existing superresolution techniques is that the envelope of performance, expressed in terms of lateral resolution of longitudinal resolution, speed, light intensity necessary for phototoxicity in the biological object, of ability to measure different objects, is very limited.

In addition, most of the methods and instruments can provide superresolution either a good lateral resolution or a good longitudinal resolution, but rarely both.

In addition, all these instruments are complex and require a highly skilled operator.

In addition, these instruments can generally observe a small part of biological specimens because of strong operational limitations, such as, for some of them, a shallow depth of field or a requirement of very high light intensities, harmful to cells.

Another problem with the methods and instruments of superresolution, is that most of them are able to recover in the illuminated volume, the attributes of a single fluorophore, but fail to recognize the presence of simultaneously several fluorophores and measuring their attributes.

An additional problem with the methods and instruments of superresolution is that these methods and instruments are presented to users and perceived by them as a general tool, able to replace the standard or confocal microscopes. However, the methods and instruments superresolution lack the simplicity, robustness, ease of use and competitive prices of standard microscopes which hinders their use as research tools or as general diagnostic tools.

Another problem with existing superresolution methods and tools is that most of these methods and tools are designed as stand-alone instruments designed to replace standard microscopes. Such an approach requires the replacement of existing instruments and the renewal of all systems and devices all the knowledge and know-how related to microscopy platforms and developed over many years.

Another problem with most methods and instruments fluorescence microscopy and superresolution is that these methods and tools are designed on a paradigm of image acquisition, the entity for which basic information is—or more images, or—or more—ROI regions—Region Of Interest bi- or three-dimensional. Algorithmic, systemic and superresolution methods described later in the context of the invention will, by their inherent flexibility, the development of new strategies of acquisition. These acquisition procedures, dynamic and selective, will be defined by an optimised sequence acquisition and interactive and deferred processing. They allow a more sophisticated optimisation of the useful information, as defined by criteria based on the shape, geometry and dynamics of one or more fluorescent objects, separately or relative one to the other.

So there is still an urgent need to provide superresolution methods and tools and algorithms methods capable of measuring with high accuracy the attributes of a fluorophore. It is also necessary to provide methods and tools to detect and quantify the presence of multiple fluorophores placed in the same volume illuminated.

Another problem with the majority of existing methods and instruments of fluorescence Microscopy and superresolution is that these methods and instruments are designed for studying samples on microscope slides. However, the confocal microscope is used today in many medical fields as instrument of in-vivo diagnosis for internal and external examinations on the human body by means of fibre optic used to illuminate and display fluorescence emitted by tissue to be diagnosed. Superresolution does not currently perform such in-vivo diagnostics. Algorithmic, systemic and superresolution methods described later in the context of the invention will allow the development of novel methods of in-vivo diagnostics which will reduce the need to take biopsies and shorten wait times for the patient.

SUMMARY OF THE INVENTION

A first aspect of the invention specifies an optical measuring process to determine the spatial or spatiotemporal distribution of a sample, the sample comprising at least one reemitting source said at least one reemitting source reemitting light as a function of projected light, onto the sample, the process comprising:

projection onto the sample, by means of optical projection apparatus, of at least two light distributions of different topological families, spreading along the same optical path, detecting of the light reemitted by said at least one reemitting source from the sample;

generating at least one optical image, from the detected light, and analysing algorithmically the optical images to obtain location information of said at least one reemitting source.

Projection onto the sample can be done sequentially or simultaneously. The reemitting source can be a point source, a structured object, for example segments of lines, circles or a continuous object.

According to an embodiment the optical projection apparatus is achromatic.

According to an embodiment the at least two compact light distributions of different topological families are projected sequentially.

According to an embodiment the generation, of at least one optical image, from detected light is carried out, each moment when the image is illuminated.

According to one embodiment said at least two compact light distributions of different topological families are created by interference between a regular wave and a singular wave, or between two singular waves, and spatial differentiation between said at least two distributions is created by varying at least one of the following parameters:

a) at least one of the parameters of the regular wave;
b) at least one parameter of at least one singular wave and
c) a phase difference between the regular wave and the singular wave or between two singular waves.

According to an embodiment the projection of light distributions of different topological families is carried out by conical diffraction.

According to an embodiment, the process also comprises modification of the projection by variation in the states of input and output polarization of at least one conical crystal performing conical diffraction.

According to an embodiment, the projection of light distributions of different topologies is carried out by conical diffraction in a thin crystal.

According to an embodiment, the process also comprises the transmission along part of the optical path of at least two compact light distributions of different topological families by fibre optic.

According to an embodiment, the fibre optic comprises a photonic fibre.

According to an embodiment, the process comprises temporal separation, by application of a physical effect, of the positioned reemitting sources, in the sample, at minimal distances from each other, by using a microscopy localisation technique.

According to an embodiment, the method also comprises the induction of the physical effect by means of an additional, regular or singular wave, by a photoactivation or photodepletion effect.

According to an embodiment, the waves of light distributions projected interact in non-linear manner, by multiphoton fluorescence effect or by Raman effect.

According to an embodiment, fibre optic is configured to transmit compact light distributions of different topological families, created previously, with different attenuation for different light distributions.

According to an embodiment, the fibre optic is arranged to create, by coupling, static or dynamic in the fibre, interaction between the light distributions injected in the fibre optic and so that light distributions emerging from the fibre differ from those injected in the fibre.

According to an embodiment, the spectral dependence of emission from a reemitting source is also modified by a Forster energy transfer effect.

According to an embodiment, said at least two compact light distributions of different topological families are col.

According to an embodiment, the achromatic unit comprises at least one light source of wavelength in a spectral band of width greater than 15% of the median wavelength of the spectral band of the achromatic optical unit creating compact light distributions, collocalised, of different topological families, spreading in the same optical path for any wavelength in the spectral band.

A second aspect of the invention specifies a measuring device for determining the spatial or spatiotemporal distribution of a sample, the sample comprising at least one reemitting source, said at least one reemitting source reemitting light as a function of the projected light, onto the sample, the device comprising:

an achromatic projection module to be projected onto the sample of at least two compact light distributions of different topological families spreading in the same optical path, a detection module capable of detecting light reemitted by said at least one reemitting source of the sample;

a generation module, capable of generating at least one optical image, from detected light; and an algorithmic analysis module capable of analysing optical images to obtain location information of said at least one reemitting source.

According to an embodiment, the projection module is configured to project sequentially the at least two compact light distributions of different topological families.

According to an embodiment, the generation module is configured to generate said at least one optical image, from detected light at each instant where the image is illuminated.

According to an embodiment:

the projection module is capable of creating said at least two compact light distributions of different topological families by interference between a regular wave and a singular wave, or between two singular waves, and spatial differentiation between said at least two distributions is created by varying at least one of the following parameters:

a) at least one of the parameters of the regular wave;
b) at least one parameter of at least one singular wave and
c) phase difference between the regular wave and the singular wave or between the two singular waves.

According to an embodiment, the projection module comprises at least one conical crystal for carrying out projection of light distributions of different topological families by conical diffraction.

According to an embodiment, the device also comprises projection modification means configured to vary input and output polarization states of said at least one conical crystal.

According to an embodiment, said at least one conical crystal is a thin crystal.

According to an embodiment, the device also comprises fibre optics for conducting transmission along part of the optical path of the at least two compact light distributions of different topological families.

According to an embodiment, the fibre optic comprises a photonic fibre.

According to an embodiment, the device also comprises a time separation module capable of temporally separating, by application of a physical effect, reemitting sources positioned, in the sample, at minimal distances from each other, by using a microscopy localisation technique.

According to an embodiment, the device also comprises induction means of the physical effect by means of an additional, regular or singular wave, by a photoactivation or photodepletion effect.

According to an embodiment, the projection module is configured to project the waves of light distributions such that they interact in a non-linear manner, by multiphoton fluorescence effect or by Raman effect.

According to an embodiment, the fibre optic is configured to transmit the compact light distributions of different topological families, created previously, with different attenuation for the different light distributions.

According to an embodiment, the fibre optic is arranged to create, by static or dynamic coupling in the fibre, interaction between the light distributions injected in the fibre optic and so that the light distributions emerging from the fibre differ from those injected in the fibre.

According to an embodiment, the device also comprises means for modifying the spectral dependence of the emission of a reemitting source by a Forster energy transfer effect.

According to an embodiment, the device comprises a microscopy device modified to make it achromatic, athermal or achromatic and athermal, by the addition of additional optical elements or by modification of the internal elements of the device.

According to an embodiment the added optical elements comprise at least one prism, a network, a lens or an additional crystal having inverse dispersion.

According to an embodiment the achromatic projection module is capable of creating at least two compact light distributions of different collocalised topological families.

According to an embodiment the achromatic projection module comprises at least one light source of wavelength in a spectral band of width greater than 15% of the median wavelength of the spectral band, and is configured to create compact light distributions, collocalised, of different topological families, spreading in the same optical path for any wavelength in the spectral band.

A third aspect of the invention relates to an optical measuring process for determining the spatial or spatiotemporal distribution of a sample, the sample comprising at least one reemitting source said at least one reemitting source reemitting light as a function of the projected light according to a determined law on the sample, the process comprising:

projection onto the sample, by conical diffraction or by means of uniaxial crystals, of at least two compact light distributions of different topological families by a common-path optical system;

detection of the light reemitted by said at least one reemitting source of the sample;

generation, of at least one optical image, from detected light, and algorithmic analysis of the optical images to obtain location information of said at least one reemitting source.

According to one embodiment the projection means are capable of creating said at least two compact light distributions of different topological families created by an interference between a regular wave and a singular wave, or between two singular waves, and spatial differentiation between said at least two distributions is created by varying at least one of the following parameters:

a) at least one of the parameters of the regular wave;
b) at least one parameter of at least one singular wave and
c) a phase difference between the regular wave and the singular wave or between two singular waves.

According to an embodiment a singular wave, originating from an optical system of common path, at a different wavelength of the regular wave, creates a depletion effect of the regular wave by either dropout of said at least one reemitting source or by transition between different excited states of said at least one reemitting source.

According to an embodiment a polarization dispersion effect is used to allow the optical system of common path to create without dynamic modification a regular wave at a wavelength and singular wave at a different wavelength.

A fourth aspect of the invention specifies an optical measuring device to determine the spatial or spatiotemporal distribution of a sample, the sample comprising at least one reemitting source said at least one reemitting source reemitting light as a function of the projected light according to a determined law on the sample, the device comprising:

at least one conical or uniaxial crystal to project on the sample, by conical diffraction of at least two compact light distributions of different topological families of common path;

detection means capable of detecting light reemitted by said at least one reemitting source of the sample;

generation means capable of generating at least one optical image, from detected light, and algorithmic analysis means capable of algorithmically analysing optical images to obtain location information of said at least one reemitting source.

According to an embodiment the device further comprises interference means for creating said at least two compact light distributions of different topological families created by an interference between a regular wave and a singular wave, or between two singular waves, and spatial differentiation between said at least two distributions is created by varying at least one of the following parameters:

a) at least one of the parameters of the regular wave;
b) at least one parameter of at least one singular wave and
c) a phase difference between the regular wave and the singular wave or between two singular waves.

According to an embodiment the singular wave, originating from an optical system of common path, at a different wavelength of the regular wave, creates a depletion effect of the regular wave by either dropout of said at least one reemitting source or by transition between different excited states of said at least one reemitting source.

According to an embodiment the device comprises polarization dispersion means for producing polarization dispersion effect for allowing the optical system of common path to create without dynamic modification a regular wave at a wavelength and a singular wave at a different wavelength.

Another aspect of the invention specifies the use of the process according to any one of the embodiments for artificial vision.

Another aspect of the invention specifies the use of the process according to any one of the embodiments for medical application.

Another aspect of the invention specifies the use of the process according to any one of the embodiments for studying biological cells.

Another aspect of the invention specifies an optical process comprising:

physical separation, by means of an achromatic optical unit based on conical diffraction and, a principal regular incident wave of at least one auxiliary incident regular wave, said at least one auxiliary incident regular wave being different relative to the regular principal wave, the regular principal wave not being modified by propagation in said achromatic unit and said at least one auxiliary regular wave, transfers a measurable part of its energy to an emerging singular wave such that the emerging singular wave includes only the energy of said at least one auxiliary regular wave; and separation of the emerging singular wave of the principal regular incident wave by a polarizing, absorbing or separating optical element.

According to an embodiment of the invention, the principal regular incident wave and said at least one auxiliary incident regular wave are polarized.

According to an embodiment of the invention, the principal regular incident wave and said at least one auxiliary incident regular wave are, at least partially, collimated.

According to an embodiment of the invention, the regular principal wave and said at least one auxiliary regular wave differ by their respective degrees of collimation.

According to an embodiment of the invention, the regular principal wave and said at least one auxiliary regular wave differ by their respective parameters of the radius of curvature.

According to an embodiment of the invention, the regular principal wave and said at least one auxiliary regular wave originate from different sources, the regular principal wave and said at least one auxiliary regular wave differ as a function of the position, lateral or longitudinal of the respective source.

According to an embodiment of the invention, the regular principal wave is originating from a source, the process further comprising the determination of the position, lateral or longitudinal of the source from intensity or phase measurements of the emerging singular wave.

According to an embodiment of the invention, the achromatic optical unit is based on the conical diffraction.

Another aspect of the invention specifies an optical device comprising:

at least one achromatic optical module based on conical diffraction or on propagation of light in at least one uniaxial crystal to produce physical separation, of a principal regular incident wave of at least one auxiliary incident regular wave, said at least one auxiliary incident regular wave being different relative to the regular principal wave, said achromatic optical module being configured so that the regular principal wave is not modified by its propagation in said crystal and for transferring a measurable portion of the energy of said at least one auxiliary regular wave to an emerging singular wave such that the emerging singular wave includes only the energy of said at least one auxiliary regular wave; and a polarizing, absorbing or separating optical element for separating the emerging singular wave of the principal regular incident wave.

According to an embodiment of the invention, the device also comprises a polarization module for polarizing the principal regular incident wave and said at least one auxiliary incident regular wave.

According to an embodiment of the invention, the device also comprises a collimation module for collimating, at least partially, the principal regular incident wave and said at least one auxiliary incident regular wave.

According to an embodiment of the invention, the regular principal wave and said at least one auxiliary regular wave differ by their respective degrees of collimation.

According to an embodiment of the invention, the regular principal wave and said at least one auxiliary regular wave differ by their respective parameters of the radius of curvature.

According to an embodiment of the invention, the regular principal wave and said at least one auxiliary regular wave originate from different sources, the regular principal wave and said at least one auxiliary regular wave differ as a function of the position, lateral or longitudinal of the respective source.

According to an embodiment of the invention, the device also comprises a measuring module configured to determine the position, lateral or longitudinal of the source of the regular principal wave from measurements of intensity or phase of the emerging singular wave.

According to an embodiment of the invention, the achromatic optical module is based on conical diffraction A goal of at least one embodiment of the present invention is to provide a technique for superresolution fluorescence microscopy in Biology and more generally to life sciences, and additionally to pharmacology, medicine and diagnostics, that will overcome the shortcomings of the prior art devices.

One of the goals of at least one embodiment of the present invention is to provide a technique for superresolution fluorescence microscopy in biology to achieve an optical system that is capable of measuring with high accuracy the attributes of a fluorophore and recognizing and measuring the attributes of multiple fluorophores located in the same illuminated volume.

Another goal of at least one embodiment of the invention is to provide a technique for superresolution fluorescence microscopy in biology to measure with high precision the attributes of a fluorophore.

Another goal of at least one embodiment of the invention is to provide a technique for superresolution fluorescence microscopy in biology that acquires and measure with great precision, the attributes of multiple fluorophores present in the same illuminated volume.

Another aspect of the invention provides a method of optical measurement and an achromatic optical unit to determine the spatial position of at least one light nanoemitter, of a structured object or continuous distribution on a sample, the method comprising:

projecting a sequence of at least two compact light distributions of different topological families on the sample;

detecting of the light reemitted by said at least one light nanoemitter, structured object or continuous distribution from the sample;

generating at least one optical image for each light distribution, from the detected light; and analysing algorithmically the optical images to obtain location information of said at least one light nanoemitter, structured object or continuous distribution.

Another aspect of the invention also relates to an achromatic optical measuring process and an optical achromatic unit for determining the spatial position of a plurality of light point sources, the method comprising the detection of the light emitted by the plurality of light point sources; and separation of the light emitted on a plurality of detectors for simultaneous or sequential detections; the proportion of light emitted by a light point source, channelled towards a specific detector, dependent on the spatial position of said light point source; and generation of optical images from detected light; and algorithmic analysis of optical images to obtain location information of the plurality of light point sources.

The description of embodiments of the invention based on confocal fluorescence Microscopy can be extended mutatis mutandis to other modalities of Microscopy, confocal or not, and to artificial Vision, whether they observe biological objects, vision artificial or other, and whether the object consists of point sources, structured objects or continuous objects.

BRIEF DESCRIPTION OF THE DRAWINGS

The invention will now be described in connection with certain preferred embodiments with reference to the following illustrative figures so that it can be better understood.

With specific reference now to the figures in detail, it is emphasized that the indications represented are presented as an example and for purposes of illustrative discussion of the preferred embodiments of the invention and are presented only in order to provide what is considered to be the description of the most useful and easy to understand principles and conceptual aspects of the invention. In this regard, no attempt is made to show structural details of the invention in more detail than is necessary for a fundamental understanding of the invention, the description taken with the drawings making apparent to experts how the several forms of the invention may be embodied in practice.

In the drawings:

FIG. 1 is a simplified perspective view of a confocal fluorescence microscope of the prior art;

FIG. 2 is a pictorial representation of a simplified superresolution fluorescence microscopy, in accordance with an embodiment of the present invention;

FIG. 3 is a simplified schematic illustration of a setup of a conical diffraction module in accordance with one embodiment of the present invention;

FIG. 4 is a simplified pictorial representation of the two measurement paradigms according to embodiments of the invention, using confocal microscopy and methodology;

FIG. 5 is a simplified pictorial representation of a particular embodiment of the method of measurement, microscopy platform SRCDP;

FIG. 6 is a simplified schematic illustration of a module lateral superresolution in accordance with an embodiment of the present invention;

FIG. 7 shows tables of light distributions of a conical diffraction module according to the polarization of the polarisers of the input and output for several values of the parameter of conical diffraction, $\rho_0$. These light distributions were calculated by simulation of equations developed by Berry, [4];

FIG. 8 is a simplified schematic illustration of a longitudinal module of superresolution in accordance with an embodiment of the present invention;

FIG. 9 is a simplified schematic illustration of a method for superresolution algorithm of fluorophores data, in accordance with an embodiment of the present invention;

FIG. 10 is a simplified schematic illustration of the calculation of descriptors;

FIG. 11 is a simplified schematic illustration of the control module of the platform SRCDP.

Figure 1:
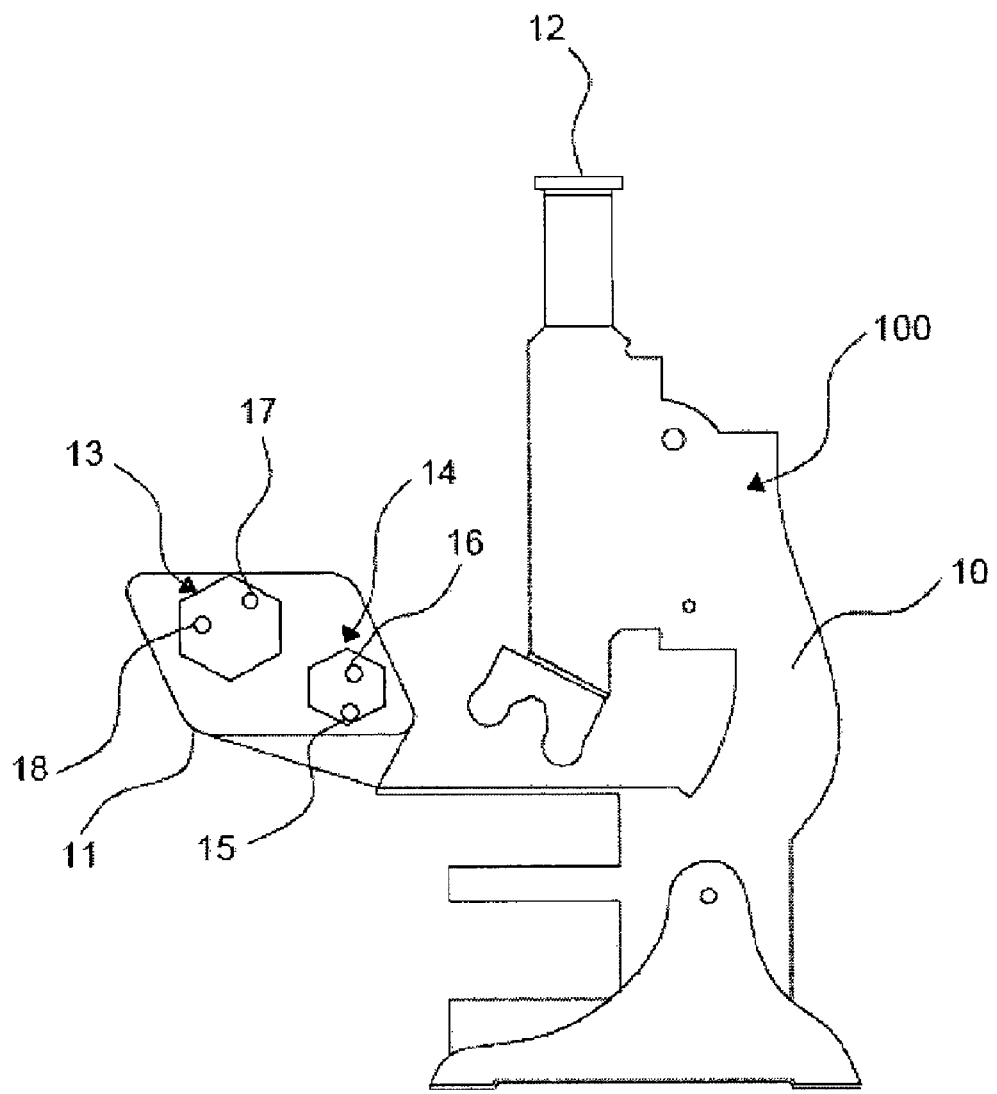

In all the figures, like reference numerals identify like parts.

Definitions and Technical Supplements

The usual definitions are used for the description: phase and polarization, polarimetry, vectors and Jones matrices, Stokes parameters and measurement techniques Stokes and Jones parameters.

The usual definitions are used in the description for the mode $TEM_{00}$ of a fibre and the English terms, "Photonic Crystal Fiber"—PCF—and "dual core Photonic Crystal Fiber".

The centre or centroid of a light distribution is the centre of gravity of the intensity. The diameter of a light distribution is the diameter of the first zero intensity, both for regular and singular waves, without taking into account the central zero of a singular wave.

Two light distributions are colocated if their centres coincide or are separated by a low spatial value relative to the dimension of the distribution of light.

In this patent application, we use the emission wavelength, as the basic metric system.

In this patent application, the usual definitions are used for the following optical components: lens whose definition has been broadened to include all optical means which transmit, refract or reflect the light, auxiliary optics—optical submodule to interface and adjust either the geometric parameters or the parameters of phase and/or polarization between two other optical sub-modules or modules-, polariser, analyser, retardation plate, beam splitter, polarizing and non-polarizing, beam combiner, polarizing and non-polarizing.

In this patent application, the usual definitions are used for azimuthal and radial polarisers. This means, implicitly or explicitly, some developments described later for azimuthal and radial polarisers, all polarizing elements variable in space.

In this patent application, the usual definitions, [5], are used for different superresolution techniques such as Stimulated Emission Depletion microscopy (STED), Ground state depletion (GSD), Photoactivated localization microscopy (PALM), Stochastic optical reconstruction microscopy (STORM), Structured illumination microscopy (SIM), Spatially Structured Illumination Microscopy (SSIM) and Forster resonance energy transfer (FRET) and Localisation Microscopy.

In this patent application, the usual definitions are used for different techniques of Microscopy, standard resolution or superresolution, fluorescent or not, such as "Computational Microscopy", "Correlative Microscopy", "Cross-platform-microscopy, FCS—Fluorescence Correlation Spectroscopy", FCCS—"Fluorescence Cross-Correlation Spectroscopy", or PCH—Photon Counting Histogram, RICS "Raster Imaging Correlation Spectroscopy" or FRAP—"Fluorescence Recovery after Photobleaching analysis".

In this patent application, the usual definitions are used for the Hough Transform.

We refer to a partial polariser to describe a component or a module whose absorption is different for the two linear polarizations—linear dichroism—or for the two circular polarizations—circular dichroism.

We refer to dynamic elements of polarization or phase, to describe the optical means, which polarization or phase vary over time in a controlled manner, discrete or continuous.

These dynamic polarization or phase elements include, but are not limited to: rotating on their axes wave plate, light valves based on liquid crystal technology, electro-optical devices, also known as Pockels cells, Kerr cells, electro-optical resonant devices, magneto-optic devices, also known as cells Faraday, acousto-optic or elasto-optic or any combination of these means.

Reference is made to dispersive polarization or phase elements to describe elements whereof the polarization state depends on the wavelength. The simplest of the dispersive polarization sub-modules is the multimode or thick wave plate. We refer to "centroid algorithm" to describe the standard procedure for measuring the centroid and possibly the width (FWHM—Full width Half Maximum) of a light distribution. Many articles have been published on this algorithm such as the article Lindegren in 1978 [6].

This algorithm has its source in Astronomy and Astrometry, and allowed the measurement of the positions of stars with high precision. This algorithm is now used throughout the optical instrumentation, including superresolution in Biology.

In this paper, the usual definitions are used for following optoelectronic components: photoelectric detector, CCD, EMCCD, CMOS SPAD—Single Photon Avalanche Diode and SPAD matrix.

We use the terms:
optical image for the spatial distribution of light intensity,
electronic image to describe the spatial distribution of charges of a CCD, of current for a CMOS, of events or for a SPAD, created by the optical image, at a given moment, in a detection plane,
digital image to describe a matrix of numbers created by conversion of the electronic image.

To simplify the reading and understanding of the text we will use the term image to the output of a single pixel detector such as PMT or SPAD, considering it as an image consisting of a single pixel.

Where no ambiguity exists, or where the distinction between the three types of images is not necessary, we will use the simplified generic term of image.

We presented the images using the terminology used for matrix detectors, such as CCD, EMCCD and CMOS. For SPAD and SPAD arrays the measurement result is an ordered list in time of photons impact detailing, for each photon, the time of impact and the position of the impact. To simplify the presentation of this document, we will include this case in our definition of images.

The images described in this document may be characterized as microimages, images of size substantially equal to a small number of the Airy disc diameters, typically less than 5 diameters, and/or low number of pixels, typically 4*4 to 32*32.

In a digital image Aj, the indices m and n represent the indices of the pixels, and the origin of the pixels will be selected as the projection of the centre of the analysis volume defined in a later paragraph.

Stokes Vector Polarimetry

Polarimetry refers to the measurement of the polarization state of incident light. The polarization state of the incident light can be described by the Stokes parameters, a set of values introduced by George Gabriel Stokes in 1852 and used in optics.

Copropagation of Two Optical Beams

Many systems and optical devices utilise two beams—or more—having different properties. The beams can either interact, or be projected sequentially or simultaneously.

In the majority of these systems and devices, the two optical paths are separated physically from each other. This physical separation creates, at the level of engineering of the system a set of constraints, which although resolvable, substantially emphasise the complexity of the system and its cost. Reference is made to systems of common path, to reference a set of devices in which the two differentiated beams spread along the same physical path, at minor variations.

Electric Field in Polar Coordinates and Angular Modes $$E(\rho,\theta)=A(\rho,\theta)\cdot\exp[i\phi(\rho,\theta)]u(\rho,\theta) \quad (\text{EQ. 1})$$

It is customary in Optics to decompose the field components, i.e. its amplitude, phase and polarization in orthogonal modes, Cartesian or polar.

Many decompositions in orthogonal polar modes, such as Galsoan, Hermite-Galsoan and Laguerre-Galsoan modes are known to experts.

We mainly use in this paper, the decomposition of the amplitude of the electric field in Hypergeometric-Galsoan modes, HyGG, with the following form:

$$A(\rho,\theta) \propto \rho^{p+|m|}\exp(-\rho^2+il\theta) \quad (\text{EQ. 2})$$

In this decomposition, $\rho$ is the radial mode and $l$ is the azimuthal order.

Singular Waves

A singular wave includes a null intensity at the centre and an azimuthal phase variation of a multiple of $2\pi$. This research topic in optics, initiated by the seminal article by J F Nye and M. Berry in 1974 [7], is now known as "singular optics". Examples of regular and singular waves are presented in the following.

Topology and Compact Light Distributions

A point-source light distribution will be considered compact if it satisfies one of the conditions of compactness defined below, as two alternative and not exclusive conditions:

either more than 75% of the energy is contained in a circle of radius less than 1.75 times the radius of Airy or a light domain, defined by a line of zero intensity and containing more than 65% of the energy is within a circle of radius less than twice the radius of Airy, We distinguish different families of point light distributions, of different topologies:

Regular distributions in their usual definition in Optics,

Singular distributions, otherwise known as optical vortices, of topological charge (azimuthal order) l, where the phase varies from 0 to $2\pi l$ around the direction of propagation, l being an integer, Amplitude distributions with azimuthal variation of order l, also referred to as Laguerre-Galsoan distribution, Polarization, and optionally phase distributions, with azimuthal variation of order l, referred to as radially polarized Laguerre-Gauss modes.

Two compact light distributions will be deemed being of different topological families if they meet at least one, and any of the following conditions:

One is regular and the other is singular,

One is point-source and the other is a ring-source,

Azimuthal orders l of the amplitude of the two different light distributions differ, Azimuthal orders l of the polarization or the phase of the two different light distributions differ.

Alternatively, two light distributions projected onto a given volume will be considered of different topologies if a significant portion of the surface illuminated together, the gradients are of reversed direction.

Light Nanoemitters

A light nanoemitter is a small secondary emitter attached to an object, and it is significantly smaller than a fraction of a wavelength, typically but not limited to a size smaller than one fifth of the wavelength; a light nanoemitter absorbs the incident energy and re-emits light at the same wavelength as the incident light or different wavelengths; the light emitted by the nanoemitter may be coherent, partially coherent or incoherent with the absorbed light. The main examples of nanoemitters are fluorophores and nanoparticles, but also include many other elements.

The definition in the context of the invention of nanoemitters light is determined by the following two conditions:

creating a secondary point-source light emitter, and predetermined positioning of the emitter with respect to an artificial, biological or organic entity.

The physical mechanisms that can create a nanoemitter are numerous, and include but are not limited to absorption, scattering or reflection, fluorescence, emission-depletion, [8], photo activation phenomena, fluorescence of two or more photons, or non-elastic scattering, Raman scattering, or any other physical mechanisms known to experts. We use the term light emission to describe the emission of electromagnetic waves by a light nanoemitter, the light being coherent, incoherent or partially coherent.

We extend our definition of nanoemitters by including scattering particles, absorbent or reflective, attached to a biological or organic entity; the action of a scattering, diffusing, reflecting or absorbing particle on the electromagnetic field can indeed be described, for an absorbing particle, following Babinet's principle, as a creation, with a reverse phase of an auxiliary secondary field emerging from the particle, superimposed on the incident electromagnetic field.

We refer to in this patent application to descriptors of a single nanoemitter to denote the set of information describing a nanoemitter as a point source at a given moment. Since the nanoemitter is considered as a point source, all the information representing it contains a limited number of parameters, namely: its position in space, its intensity, its spectral characteristics of the intensity, coherence, phase and polarization of the light emitted by the fluorophore as a function of the incident light.

Reference is made in this patent application to the descriptors of a structured object. For example, for a uniform line, all of the information representing it contains a limited number of parameters, either its orientation in space, its intensity, spectral characteristics, intensity, coherence, phase and polarization of the light emitted by the object, as a function of incident light.

For continuous distribution, the object is represented, as usual in image processing, by a matrix of intensities.

However, in most cases, and in the description of the invention, we refer, under the designation of descriptors, a subset of descriptors of a nanoemitter including its geometric position, its intensity, and the type of fluorophore, whether several populations of light nanoemitters, differentiated for example by their emission spectrum, are present in the same sample. This simplification used in the description does not alter the scope of the invention which will include in its scope all the descriptors of light nanoemitters.

To simplify the understanding of the context of the invention, the following description refers only the simplest case, one in which the nanoemitter is a fluorophore and physical interaction is the one photon fluorescence. However, this description should be understood as a simplified illustration of a general description of the methods and concepts applicable to all light nanoemitters mentioned previously or known to experts, regardless of the underlying physical phenomenon.

It is striking that the nanoemitter samples the incident light intensity field at a three-dimensional position accurately without influence of the complete spatial distribution of the incident intensity. We will reference this remarkable property in this patent application as the sampling ability of light nanoemitter.

However, the preferred embodiment of the invention as described also measures structured objects and continuous distributions having no sampling capacity of the light nanoemitter.

We refer again to the FIG. 1 which represents a set of nanoemitters or structured objects positioned on a given biological object, 15 and 16 on the one hand and 17 and 18 on the other hand. Alternatively, the light emitted can consist of continuous distribution, not shown in FIG. 1, or in any combination of nanoemitters, structured objects or continuous distributions. The set of nanoemitters, structured objects or continuous distributions is referenced as a set "bright biological objects", they represent a map of the biological object, in the sense defined by Alfred Korzybski in general semantics. However, it is common practice to simplify the description, reference the object as the luminous-biological object itself, when no ambiguity can arise. The luminous biological object contains information that is relevant to the biological object, mainly spatiotemporal information, the object position and orientation with respect to time, and morphological information, for example in the case of division of a cell in two.

The measurement system according to at least one embodiment of the invention will calculate the measured map, and carry out evaluation of the descriptors of any combination of nanoemitters, structured objects or evaluation of the spatial distribution of continuous distributions. This measured map differs from the original map, due to noise, measurement conditions, the system limits or measurement uncertainty. This information of the measured map can be developed later into different levels of abstraction. This first level of abstraction, which presents the results of direct measurement, contains a priori no biological information but is the results of a physical measurement described by nanoemitters, structured objects or continuous distributions which could also represent any marked entity.

The second level, the geometric level of abstraction, structures nanoemitters of structured objects or continuous distributions in the form of geometric objects. It comprises a description of luminous objects and their dynamic characteristics, such as their position or orientation, or their morphology. At this level, the information is still physical and geometric information describing a set of objects. The geometrical information uses the measured card and auxiliary information, potentially external to the system, the relation between light spots and objects.

The biological level of abstraction, allows some understanding of the biological reality through a constitutive relationship between objects measured and corresponding biological entities. It contains a set of information on the biological object, mainly the position and its dynamics, its shape and morphology. The biological information uses the measured card and the geometrical information and auxiliary information, potentially external to the system, the relation of the light spots and objects with biological entities. A number of conclusions on the biological functionality of the sample can be obtained at this level.

The level of functional abstraction allows apprehension of the biological reality. It consists of functional information, decorrelated from geometric information, and responding to interrogations in terms and biological jargon, such as: "has the virus penetrated the cell?".

An additional level of information can be defined including the control and instrumentation process; in fact, a more evolved control and instrumentation process can be defined to reach more structured biological information, via automation of the process of data acquisition. An example of such processes is described by Steven Finkbeiner, under the name of "Robotic Microscopy Systems", [9].

This description of levels of abstraction, defined in this application, has been redacted, for the sake of simplicity, for Biology. It is applicable, mutatis mutandis, to all fields of Vision, biological and medical, artificial and industrial.

Conical Diffraction

Conical diffraction or refraction is an optical phenomenon predicted by Hamilton [10] in 1832, and two months later confirmed experimentally by Lloyd [11]. Conical diffraction describes the propagation of a light beam in the direction of the optical axis of a biaxial crystal.

In fact, in a biaxial crystal, the optical axis is positioned in the plane created by the crystallographic axes x and z; the ankle relative to the axe z is $\theta_0$, depending on the three indices of refraction as per the law, $$\tan\theta_0 = \sqrt{\frac{n_1^{-2} - n_2^{-2}}{n_2^{-2} - n_3^{-2}}}.$$

Hamilton predicted that the light emerges in the form of a hollow cone of rays. Conical refraction is an important phase in the history of science and has played a role in the demonstration of the theory of electromagnetic waves.

A renewed interest in the conical diffraction occurred in the last years of the twentieth century has led to a complete theory by Berry and al. [4, 12, 13] validated experimentally in 2009 [14]. Here we follow the theory, terminology and definitions of Berry, including, from this point, the name change of the physical effect, using the more rigorous term of conical diffraction.

However, it is important to note that the term <<conical diffraction>> is also used for two other techniques not relating to the technique we describe:

Oblique incidence diffraction is also called conical diffraction

"Conical diffraction mounting" references mounting a diffraction network in which the network is mounted on a curved surface.

Conical diffraction has attracted considerable theoretical and experimental, but "no practical application seems to have been found" [15].

Historically, conical diffraction was observed in biaxial crystals. We refer to a conical crystal to describe a biaxial crystal inorganic or organic, exhibiting the phenomenon of conical diffraction. Some non-limiting examples of biaxial crystals include Aragonite, KTP, KTA, KBiW, LBO, KNbO3, MDT, YCOB, BIBO, DAST, POM, NPP, LAP, LiInS2 and LiInSe2.

Other effects exist, creating inherently weaker conical diffraction effects or creating conical diffraction along a short optical path. These effects include polymers, liquid crystals and induced externally birefringence effects. The polymers include but are not limited to: stretched polymer sheets and cascade polymerisation[16], liquid crystals include but are not limited to: thermotropic biaxial nematic phase[17], the external effects induced birefringence include, but are not limited to: applying an electric field creating an electro-optical effect on a non-centrosymmetric cubic crystal, [18], and the photo-elastic modulator, [19].

The phase in the vortex created by conical diffraction is a geometric phase and is therefore intrinsically achromatic. The additional chromatic effects are dispersion of the optical axis and dependence on the different parameters present in the equations of conical diffraction as a function of the wavelength.

The dispersion chromatic of the optical axis creates an angle of the optical axis of the crystal, dependent on the wavelength, relative to the optical axis of the system. It is due, in the majority of cases, to dispersion of the refraction indices.

The wavelength indices depend on the wavelength, as per Sellmeier equations. The angle of the optical axis varies therefore as a function of the wavelength, and it creates an angle of chromatic inclination of the optical axis in the plane created by the crystallographic axes x and z.

It depends considerably on the type of crystal. In an MDT crystal, the most available achromatic crystal in the visible spectrum, the direction of the optical axis varies by less than 0.1 degrees between 540 nm and 700 nm. In a KTP crystal, the most achromatic crystal in the telecommunication IR, the angle varies by 0.05 degrees, between 1.350 nm and 2.100 nm, and less than 0.02 degrees on the telecommunication window—1450 nm to 1650 nm. On the other hand, $\theta_0$ can vary considerably as a function of the wavelength in some organic crystals such as DAST.

The compensation of chromatic dispersion of the optical axis can be carried out using the geometric optic. The chromatic dispersion of the direction of the optical axis can be compensated by using the natural dispersion of glass or other optical materials, or by using networks or prisms. The achromatisation procedure does not differ, in this case, from the standard procedure of correction of any chromatic aberration on geometric optics. This procedure can be designed and optimised using one of the commercial optical software packages available in defining adequate target functions.

A different achromatisation concept is based on the use of two different materials, having effects of inverse conical diffractions, at high and low chromatic dispersions. The dependence of different parameters present in the equations of conical diffraction as a function of wavelength modifies the parameters of efficacy of the effects of conical diffraction.

For conical linear crystals, defined later, the fundamental transfer function is identical to and trivially independent of wavelength. The vortex transfer function can be shown as a factor of chromatic efficacy equal to $\tau(\lambda)$.

For sinusoidal conical crystals, defined later, the behaviour is different to that of conical linear crystals: the fundamental wave depends on the wavelength and the wave vortex is almost independant of the latter. In fact, simulations show that the form of the wave vortex is modified only slightly by a variation of the parameter, $\theta_0$ from 0.5 to 0.75. By contrast, the form of the fundamental wave depends on wavelength and this effect must be taken into account in the design of systems using the two waves, fundamental and vortex.

Figure 3:
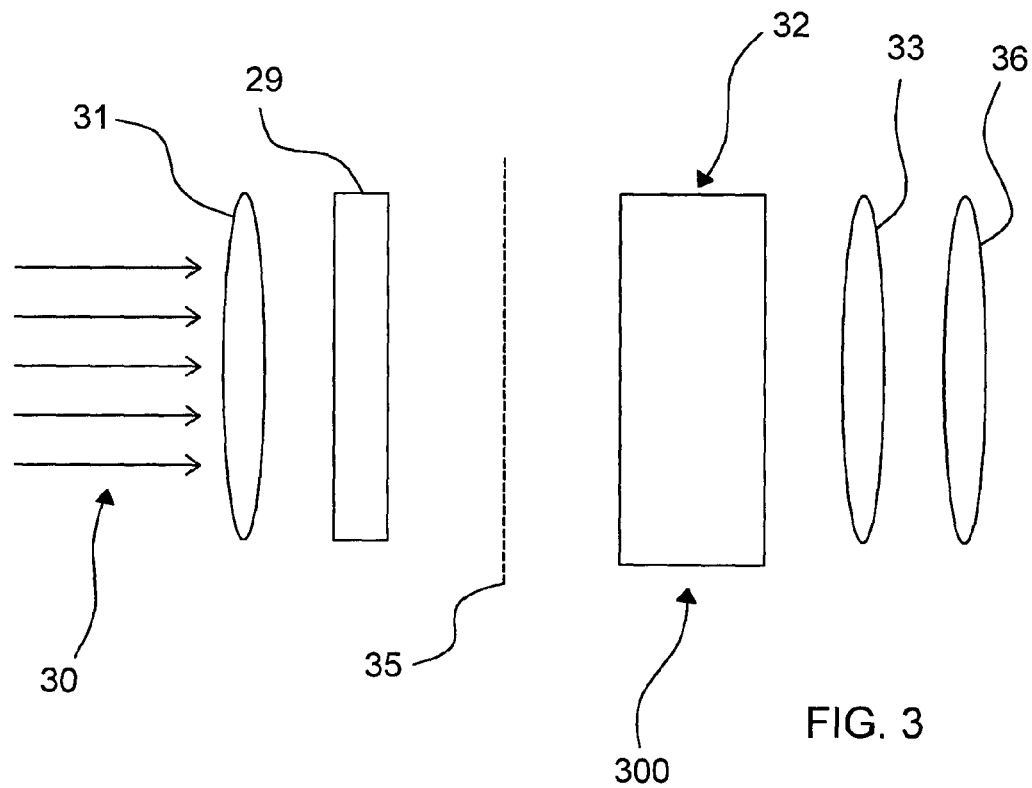

We refer now to FIG. 3, which is a simplified schematic illustration of a configuration of a conical diffraction module 300, in accordance with an embodiment of the present invention.

Incident light, 30, is assumed to be parallel, although other conditions can be adapted using simple optical means. The setup itself comprises a first lens 31, a conical crystal 32 and an optional lens 33. The first two lenses 31 and 33 are preferably configured in the form of a Kepler telescope 1:1. The numerical aperture of the first lens 31 in the image space, represented below by $U_0$, determines the parameters of the conical [diffraction] effect through the conical radius, defined below. An imaging plane conical, 35, is placed in the focal plane of the first lens 31, a partial polariser part 29, described above, may also be added. A focusing lens, 36, determines the scale of the final light spot. It can be a microscope objective external or can be merged with the second lens 33, as implemented in another embodiment of this invention. The distribution of the light projected onto the sample is in a first approximation, neglecting the vectorial effects, a reduced image of the light distribution in the image plane. The influence of vectorial effects will be discussed below. The scale ratio is determined for a microscope objective by the magnification.

Given the spatial variable, R, the conical imaging plane, and the wave vector, U, represented by cylindrical coordinates R, $\theta_R$ and U, $\theta_u$ and given $\lambda$, the wavelength of light.

The behaviour of the electric field emerging from the conical crystal 32 is fully characterized by a single parameter, the radius conical $R_0$; the conical radius depends on the material and the thickness of the crystal.

We introduce standardized parameters for the description below of the light distribution, to be valid in both conical imaging plane and at the focus of the microscope objective, in the limits of the scalar theory of diffraction.

The normalized radial position, $\rho$, the wave vector normalized, u, represented by cylindrical coordinates by $\rho$, $\theta_R$ and u, $\theta_u$, and the normalized radius conical $\rho_0$ are given by:

$$\rho = 2\frac{R}{\lambda}U_0, u = \frac{U}{U_0}; \rho_0 = 2\frac{R_0}{\lambda}U_0. \quad (EQ.\ 3)$$

$$\rho = 2\frac{R}{\lambda}U_0, u = \frac{U}{U_0}; \rho_0 = 2\frac{R_0}{\lambda}U_0. \quad (EQ.\ 4)$$

$U_0$ being the numerical aperture of the system. For $\rho_0 < 2$, we refer here to a thin conical crystal, for $\rho_0 \ll 1$, we refer here to the form of a linear thin conical crystal and for $\rho_0 < 0.5$ to a thin sinusoidal conical crystal.

The wave emerging crystal thin conical, $E(\rho, \theta_R)$, expressed in normalized coordinates, is constituted by the superposition of two waves, referred to herein as the fundamental wave, $E_F(\rho)$, a regular wave, and vortex wave, $E_V(\rho, \theta_R)$, a singular wave; these two waves are coherent one with another, colocated, and circularly polarized with an inverse direction of chirality:

$$E(\rho, \theta_R) = \quad (EQ.\ 5)$$
$$E_F(\rho) + E_V(\rho, \theta_R) = E_F(\rho)\begin{pmatrix}1\\-i\end{pmatrix} + F_V(\rho)\exp(-i\theta_R)\begin{pmatrix}1\\i\end{pmatrix}$$

$$E(\rho, \theta_R) = \quad (EQ.\ 6)$$
$$E_F(\rho) + E_V(\rho, \theta_R) = E_F(\rho)\begin{pmatrix}1\\-i\end{pmatrix} + F_V(\rho)\exp(-i\theta_R)\begin{pmatrix}1\\i\end{pmatrix}$$

In this equation, $E_F(\rho)$ is the scalar fundamental amplitude, $F_V(\rho)$ is the reduced scalar magnitude of vortex and they are given by:

$$E_F(\rho) = 2\pi \int du\ u\ \cos(\rho_0 u) J_0(\rho u); F_V(\rho) = 2\pi \int du\ u\ \sin(\rho_0 u) J_1(\rho u). \quad (EQ.\ 7)$$

For a thin linear conical crystal, the fundamental wave can be approximated by an Airy disk and the vortex wave can be approximated to a linear vortex, represented by:

$$F_V(\rho) = 2\pi\rho_0 \int du\ u^2\ J_1(\rho u). \quad (EQ.\ 8)$$

Assuming that the action of partial polariser, 29, is the scaling of the vortex wave by a parameter $\alpha$, the Stokes parameters can be deduced from the above equations, $\beta$ being the angle of the linear polarization:

$$S_0 = (E_F(\rho))^2 + (\alpha^2 F_V(\rho))^2$$

$$S_1 = 2\alpha E_F(\rho) F_V(\rho) \sin\theta_R;\ S_2 = 2\alpha E_F(\rho) F_V(\rho) \cos\theta_R;$$

$$S_3 = (E_F(\rho))^2 - (\alpha^2 F_V(\rho))^2$$

$$\beta = \theta_R; \quad (EQ.\ 9)$$

We use the terms of "sparse object" to describe a set of light emitting point like emitters, of a number less than twelve, positioned in a volume whose size in each dimension is less than 3 wavelengths, at the wavelength of transmission or at the wavelength of the reflection of the emitters. The volume of a size less than 3 wavelengths that contains the sparse object is referred to as an analysis volume of reduced size.

We will use the term of continuous object to describe a set of light point or continuous emitters which do not fulfil the conditions described earlier in the definition of the sparse object.

Figure 4A:
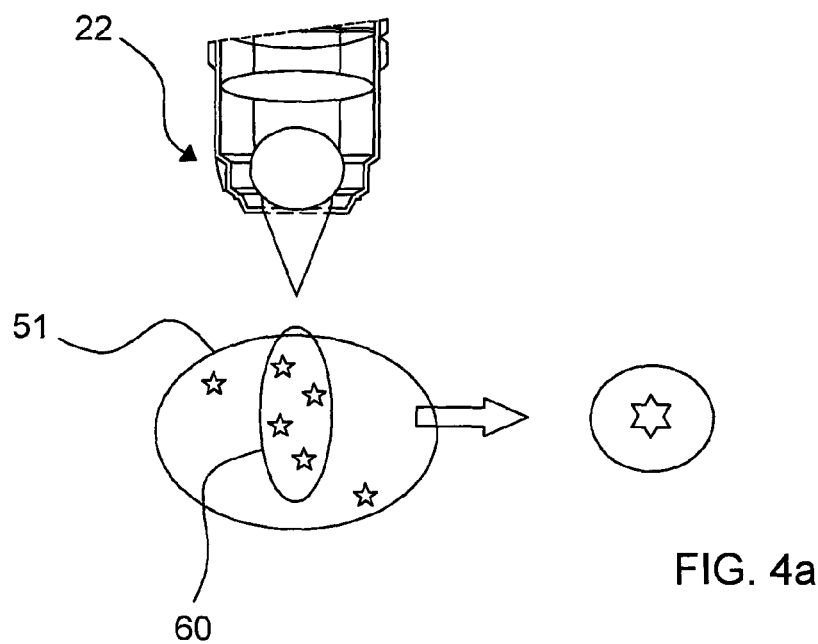
Figure 4B:
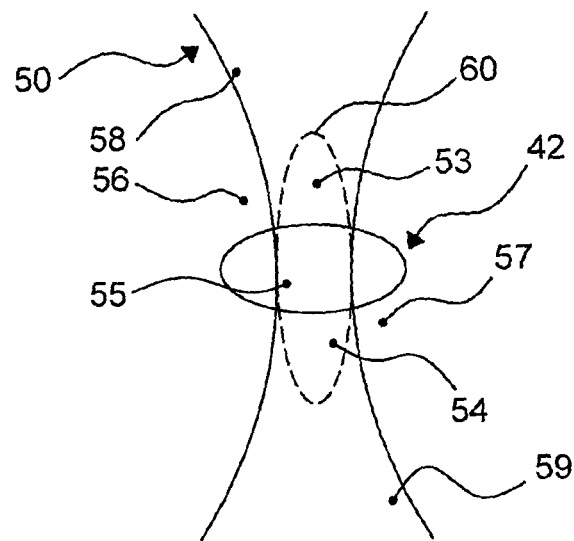
Figure 4C:
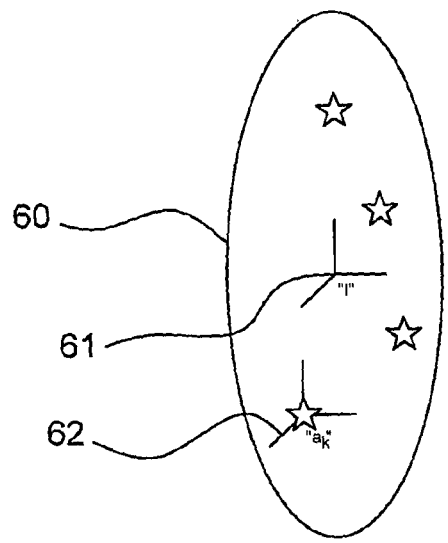

We refer now to FIGS. 4a to 4c, which are a simplified representation of the concept of volumic containment in the confocal microscope.

The functionality of the volumic containment is limited in all three spatial dimensions, the observed region of the sample volume to a size as small as possible, analysis volume. The functionality of the volumic containment limits the analysis volume by the combination of two effects: the confinement of the light projected onto a small area, ideally the size of the Airy spot, 50, and the elimination of defocused light by the confocal hole, 28, of FIG. 2. The superposition of these two effects creates a small volume, the analysis volume, 60. This volume determines the size of the elementary cell detected by the system.

Figure 2:
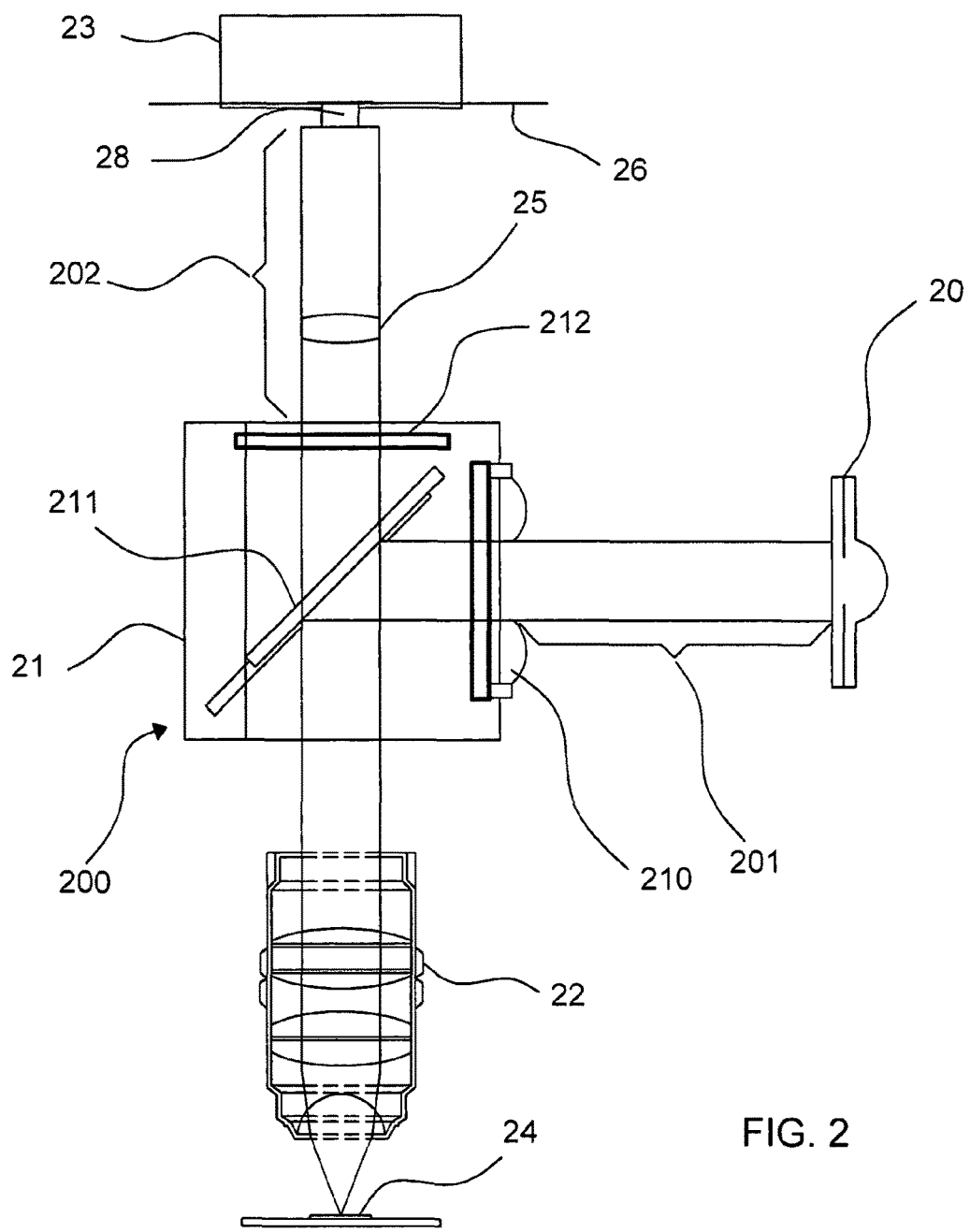

Consider a sparse or continuous object, 51, consisting of a plurality of nanoemitters, 53 to 59. The nanoemitters from 53 to 55 positioned in the test volume 60, and only they are both excited by the light source and the photons emitted by them arrive at the detector module. The nanoemitters not located in the cone of illumination, 56 and 57 are not illuminated by the incident light. The light emitted by the nano emitters 58 and 59, located at the conjugate plane of the confocal hole, 28 of FIG. 2, is blocked almost entirely by the confocal hole, 28 FIG. 2.

Two different Cartesian coordinates are defined in the system, FIG. 4c:

The reference "i": The axes referenced "i" represent a Cartesian reference system centred on the centre of the analysis volume, 61.

The reference "a": the axes referenced "a" represents a Cartesian reference centred for each light nanoemitter on the nanoemitter considered as a discrete point, 62.

When using another embodiment of the invention, described later, if a vortex is projected onto the sample being analysed, the centre of the vortex will be generally defined as the centre of the analysis volume.

The confocal microscope limit the analysis volume using the volumic confinement described above. The volumic confinement volume is obtained by the combination of two effects: confinement of the light projected on a small surface, ideally of the size of the Airy disk, 50, and removal of defocused light by the confocal hole, 41. The superposition of these two effects creates a small volume, the analysis volume 60. This volume determines the size of the elementary cell detected by the system.

At least one embodiment of the invention uses conical diffraction to realize the fundamental optical modules of the technique. However, alternative implementations, replacing the modules based on conical diffraction by modules based on other optical concepts, are able to provide the same functionality. They are part of the scope of this invention. Alternative optical concepts include but are not limited to uniaxial crystals, sub wavelength gratings, structured laser modes, holographic components and other techniques known to the skilled in the art.

The concepts, techniques and optical and optoelectronic devices are described for example in the book written by D. Goldstein, "Polarized Light", [20], the "Handbook of Confocal Microscopy", [21], "Handbook of Optics", [22].

Optical Semaphore

In this embodiment of the invention we use the term optical semaphore to describe an optical, passive or active element capable of channelling incident light to different channels or detectors as a function of a property of light. The simplest case is a dichroic blade which separates the light into two channels as a function of wavelength.

In this embodiment of the invention we use the term, "Position dependent Optical Semaphore"—PDOS—or optical semaphore dependent on position—to describe an optical semaphore which channels light as a function of the position of the emitter point. The PDOS will be determined by a series of transfer functions, $T_i(x,y,z)$ dependent, for each channel or detector i, on the position of the emitter $(x,y,z)$, in a reference volume. The order of the PDOS will be the number of channels or detectors. The PDOS will be <<without loss>>, lossless in English, in an analysis volume, if the sum of the transfer function, $T_i(x,y,z)$ is equal to the unit in the analysis volume.

The confocal hole, described by Minsky, [23], is considered in this embodiment of the invention as a degenerated PDOS of order 1.

In the majority of cases dependence of the PDOS is a complex function of the lateral and longitudinal positions. However, in embodiments of the invention we use the term, "Longitudinal Position dependent Optical Semaphore"—LPDOS—or optical semaphore dependent on the longitudinal position—to describe an optical semaphore which channels light as a function of the longitudinal position of the emitter point. The LPDOS will be determine by a series of transfer functions, $T_i(z)$ dependent, for each channel or detector i, on the longitudinal position of the emitter $(z)$, in a reference volume. The order of the PDOS will be the number of channels or detectors. The LPDOS will be "without loss", lossless in English, in an analysis volume, if the sum of the transfer function, $T_i(z)$ is equal to the unit in the analysis volume. The LPDOS will be often coupled to a stop, limiting the lateral field of the system.

Transmission by Optical Fibres

A principal use of fibre optics is the exclusive transmission of the $TEM_{00}$ mode. However, some configurations of fibre optics, mainly but not exclusively based on fibres called "Photonic Crystal Fiber"—PCF—allow simultaneous transmission or not of more complex modes, including vortex modes, having equal voracity or less than 2, [24]. It would therefore be possible to deport the optical distributions created by conical diffraction by means of fibre optics, allowing major simplification of the optical system.

The possibility of deporting the optical distributions created by conical refraction by means of fibre optics allows application of the embodiments of the invention to many additional applications, for example but non limited to gastric or gastroenterological observation, and to observation of the colon and urinary tracts.

Also, some fibres "dual-core photonic crystal fibers", [25], allow interaction between two modes, one of them being a vortex, and providing an additional physical mechanism to create diversified transfer functions.

Measurements of Several Wavelengths

In embodiments of the invention the object can be lit by monochromatic light and by using for example a classic laser or a monochromatic lamp. This configuration is simple, since one of the main parameters of the system is fixed and clearly determined.

However, in other embodiments of the invention the object can also be lit by several wavelengths, either discretely using several lasers for example, or continuously using a lamp or a laser having a wider spectrum for example.

Many existing superresolution systems measure simultaneously or sequentially at several wavelengths. In fact, it is possible to mark similar or different elements with fluorophores having different spectral, responses so they can be recognised and separated. It is important to present the two different cases:

The use of fluorescent markers, emitting at two different wavelengths, excited by the same wavelength;

The use of fluorescent markers emitting at two different wavelengths, excited by two different wavelengths.

It should be noted that in the case of the use of fluorescent markers, emitting at two different wavelengths, excited by the same wavelength, the problem of recalibration between the measurements of a wavelength relative to the second, are intrinsically inexistent since the superresolution position information is derivative of the projection of light, which is perfectly identical.

This allows relative calibration of the position of fluorophores at two different wavelengths, with precision limited only by the experimental calibration system, eliminating the major problem of recalibration between two images of different wavelength.

The possibility of achromatising optical systems based on conical diffraction makes a tool of choice for implementation of optical systems, of common path, for many applications, and more particularly for embodiments of the invention described.

Achromatisation is also possible for optical systems based on uniaxial crystals, and for almost all alternative implementations of this invention, with, for each of them, almost more or less substantial complexity.

Other existing fluorescence systems utilise light having a wider spectral content to reduce artefacts, and principally the effects of speckle.

Equally, the spectral properties of fluorescent proteins measure the potential of intracellular molecular interactions by using the Forster energy transfer technique—Forster (Fluorescence) Resonance Energy Transfer (FRET).

Non-Linear Interactions

Non-linear interaction between two light beams in a material milieu is a superresolution method described for example by Hell, [8] or by Schermelleh et al. [3]. These non-linear interactions include but are not limited to dual-photon interaction phenomena, emission-depletion effects on which STED or GSD technologies are bases, and photoactivation effects on which stochastic and natural techniques are based or those caused by an additional optical beam, such as "stochastic blinking", PALM and STORM.

Information

Information a Priori and Complementary Information

Embodiments of the invention described enable integration and merging of additional information external to the platform described, optical or contextual, to obtain improvement in precision of information taken from the sample for any one of the cited levels of abstraction: map, the geometric level of abstraction, the biological level of abstraction and the functional level of abstraction.

More generally, spectral diversity, information obtained at several wavelengths, polarization diversity, and information obtained by projecting different states of polarization, expands the extent of available information.

The fact that the absence of energy, for example in the case of the zero of the vortex, is pertinent information, opens additional possibilities to the acquisition of information without "cost" in a number of photons. This situation has major importance for detection of low fluorescence phenomena, such as for example auto fluorescence.

We introduce the concept of optical integral information, information which could be retrieved from optical measurements or by electromagnetic waves, on a target, by an observer, from a given viewpoint. This information contains many parameters of the object, related to its position, the materials which comprise it, its temperature, or its orientation.

Optical integral information on the contrary does not contain information on regions of the object having no optical path to the observer, for example an element positioned in an opaque box, or physical information which has no optical transcription.

Superresolved Measurements and Diffraction Limit

It has been long considered that optics intrinsically limited resolution of any optical system, via the diffraction limit. The appearance of superresolution techniques—in different fields and under different names—has shown that it is possible to exceed this diffraction limit, by different means.

Embodiments described in this invention, such as detection of the presence of two points of the same intensity, by projection of a vortex at the centre of gravity of light distribution created by the fundamental wave, are not limited in resolution a priori and could ideally—with an infinite number of photons—obtain any resolution, as will be described later for a specific case.

Acronyms

We use in this patent application the acronym, SRCD, "Super Resolution using Conical diffraction" to name the platform, modules and systems specific to the preferred implementation of this invention.

We use in this patent application the acronym PSIT "Projected Sequence of Intensities with various topologies".

We use in this patent application the acronym, PDOS, "Position Dependent Optical Semaphore".

The SRCDP platform, "Conical diffraction using Super Resolution Platform" is a platform for microscopy, implementing the measurement methodology and using optical modules based on conical diffraction. SRCDP platform is the preferred implementation of the measurement methodology.

We use in this patent application the acronym LatSRCS to name the optical module implementing the PSIT method for the preferred implementation of this invention.

We use in this patent application the acronym LongSRCS to name the optical module implementing the preferred implementation of the method PDOS of this invention.

Some embodiments of the present invention comprise a new measuring methodology; the measurement methodology, and a coherent set of systemic and algorithmic method, hardware tools, software tools and algorithms for its implementation The measurement methodology according to embodiments allows acquisition of nanosized optical data and image superresolution. The measurement methodology is primarily, but not exclusively, used for the measurement of super-resolved biological samples data marked with nano emitters.

The measurement methodology according to this embodiment of the invention can be implemented using the different methods of measurement and processing algorithms, described below. Among other things, the measurement methodology can be implemented together or separately using two new complementary measurement methods, referred to as PSIT and PDOS.

Some embodiments of the invention also relate to a system—a platform for microscopy, the SRCDP platform—implementing the methodology of measurement using the measurement PSIT and PDOS methods. The SRCDP platform is the preferred implementation of the measurement methodology.

The SRCDP platform, described in detail hereinbelow, comprises mainly two hardware modules, two new and complementary optical modules the LatSRCS and Long-SRCS optical modules, mounted on a microscope, and an algorithmic module SRCDA, to reconstruct the information of the superresolved sample. Additionally, the SRCDP platform includes an improved detection module, a control module of the system, and software support.

The measurement methodology uses both measurement methods, the PSIT and PDOS methods. However, in some applications, the use of both methods may not be necessary, we will refer in this case to the simplified measurement methodology, which is part of the scope of this invention.

Some embodiments of the invention also relate to methods of using the measurement methodology for measuring distribution of nanoemitters and fluorophores, and monitoring in two or three dimensions of nanoemitters.

In addition, certain embodiments of the invention relate to a large number of variants of implementations of the methodology and PSIT and PDOS methods, platform SRCD, optical modules and LatSRCS LongSRCS and algorithmic SRCDA.

The Measuring Methodology Paradigm

The functionality of the confocal microscope described by Minsky [19], and explained previously, is limiting in three spatial dimensions, the observed region of the sample volume to a size as small as possible, volume analysis.

As a corollary, in a confocal fluorescence microscope, the information retrieved is a single value of intensity for the entire volume analysis, considered as a single entity.

More clearly, detailed information on the position of nanoemitters within the analysis volume is not available, a priori, in a confocal microscope. It was generally agreed that no additional optical information could be created that would allow further discrimination within the illuminated volume.

Figure 4D:
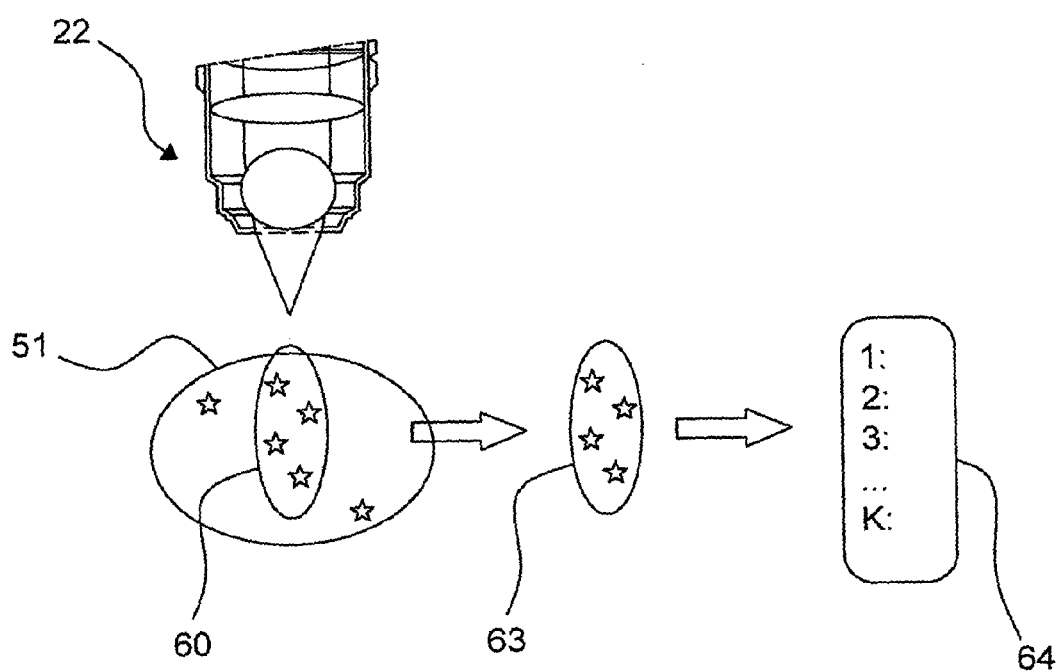

Referring now to FIG. 4d, which is a simplified conceptual representation of the paradigm of the measurement methodology according to at least one embodiment of the invention. The paradigm of this methodology is much more ambitious than that of the fluorescence confocal microscope, shown schematically in FIG. 4a.

In FIG. 4d, a test volume 60 is created at the focal plane of the microscope objective, 22; it contains a sparse object, 51, consisting of several nanoemitters, 53 to 59; the result of the system implementing the method is a reconstructed sparse object, 63, a list of nanoemitters and a list of their attributes, 64. However, the use of a parsimonious object in FIG. 4d is by way of illustration and this figure would have been perfectly able to represent a continuous object, mutatis mutandis.

A system implementing the method according to at least one embodiment of the invention is capable of recovering independently and accurately the attributes of several nanoemitters in a luminous volume of dimensions similar to those of confocal microscopy. To achieve this goal, the methodology according to some embodiments of the invention is designed to create optically for each illuminated volume, a large amount of information in both time and spatial domains.

The most developed process of the measurement methodology, according to an embodiment of the invention, can be segmented into seven steps, five optical steps, an opto-electronic detection step and an algorithmic step.

Optical Steps:
Projection of a sequence of compact light distribution of different topologies on the analysis volume Emission of fluorescent light by nanoemitters
Imaging of fluorophores in the focal plane
Separation of the reflected light detected in several independent channels simultaneously and/or sequentially
Optional limitation in the focal plane of the analysed light
Detecting step
Detecting the light intensity by one or more point like or matrix photodetectors.
Algorithmic Step:
Or
Reconstruction of the list of nanoemitters, constituting the sparse object, and their attributes from the set of the detected images,
Reconstruction of the spatial distribution (or spatio-temporal, if the dynamics are considered) constituting the continuous object, from the set of images detected.

According to another embodiment of the present invention, the measurement methodology consists in the realization of optical steps, previously described and omitting either the first is or the fourth optical step.

The compound optical process that implements the methodology: performing a series of optical measuring processes, controlled by the control module of the system, by varying the sequence of illumination and/or the functionality of the channels and/or the position of the sequence illumination as function of measured data or of external information. An example of compound optical process implementing the methodology according to an embodiment of the invention will be detailed below.

PSIT Measuring Method

A method of measurement PSIT according to one embodiment of the invention, projects a sequence of light distributions of different topologies, on the analysis volume.

The measurement method PSIT, performs the following functions:
Projection of a sequence, the emission sequence of compact light distributions of different topological families on a sample, and
For each compact light distribution:
emission of light by nanoemitters on the sample,
creation, by means of the microscope optics, of an optical image.
acquisition of the optical image on a photodetector and creation of a digital image.
In more detail, it is noted that:
The transmission sequence comprises at least two point like light distributions, of different topological families.

The transmission sequence is projected onto a biological sample labelled with nanoemitter. The light emitted, emerging from each nanoemitter, is dependent for each nanoemitter of the light intensity, in the incoherent case or on the electromagnetic field, in the coherent case, incident on the three-dimensional spatial position of the light nanoemitter, the aforesaid light sampling property of the nanoemitter discussed previously.

For each light distribution pattern of the transmission sequence projected on the sample, an optical image is created. The set of images corresponding to all the light distributions of the transmission sequence is referred to as the sequence of images.

The PSIT method according to this embodiment can acquire mainly lateral information, that is to say, the lateral position of each of the nanoemitters.

In a preferred embodiment, the PSIT method is implemented by the projection of light distributions of different topologies created by conical diffraction and modified by a variation of the polarization states of input and output.

PDOS Method

A PDOS method according to an embodiment of the invention includes the distribution of an "optical semaphore" of the light reemitted by the nanoemitters between at least two detectors.

Ideally, the function of the optical semaphore is to separate different areas of the test volume on different detectors. Practically, the optical semaphore creates, for each detector, a transfer function of the light emitted by a light nanoemitter, depending on the position in space of the light nanoemitter and different for the different detectors.

In a preferred embodiment, the PDOS method is implemented to separate on different detectors the collimated light, emerging from nanoemitters positioned at the focal plane of the lens, from non-collimated light emerging from nanoemitters lying within or beyond the focal plane.

The PDOS method, in its preferred embodiment, allows acquiring essentially longitudinal information, that is to say, the longitudinal position of each of the nano emitters.

Mathematically, the method according to some embodiments of the invention provides a transfer function converting the spatial distribution of the nanoemitters in space in unprocessed information consisting of a set of images. The algorithmic performs the inverse operation: it reconstructs the spatial distribution of the nanoemitters in space from the set of images in the raw information.

Information in Embodiments of the Invention

The intermediate result, the raw information is obtained at the end of the detection step. Raw information comprises a set of images Aop(m, n) representing for the o light distribution, the image from the detection channel p.

As in a confocal microscope, the measurement process analyses a small volume in a much larger object. It will therefore require the addition of additional modules, similar to those of a confocal microscope including a scanning process, a software module integration, analysis and visualization of data points in surfaces and/or three-dimensional objects.

In mathematical terms the algorithm solves an inverse problem or parameter estimation. The model equations are known and a model, parametric or not, is used a priori on the configuration of nanoemitters. The most natural model consists of supposing a low number of nanoemitters (sparse object), but continuous models can also be used, supposing the presence of unidimensional structures (lines, curves) or specific patterns. So we can use all the mathematical procedures known to experts for solving inverse problems and parameter estimation. We describe later an example of algorithm adapted specifically to the measurement methodology according to an embodiment of the invention.

In addition, we present, for its symbolic value, a new solution to the problem of discrimination of two points located at a small distance from each other. This problem studied by Lord Rayleigh, is the base of the resolution criterion in many areas of Optics.

It has thus been described, rather broadly, the characteristics of the embodiments of the invention in order that the detailed description thereof may be better understood, and in order that the present contribution to the art may be better appreciated. Many additional features of the invention will be described below.

Figure 5:
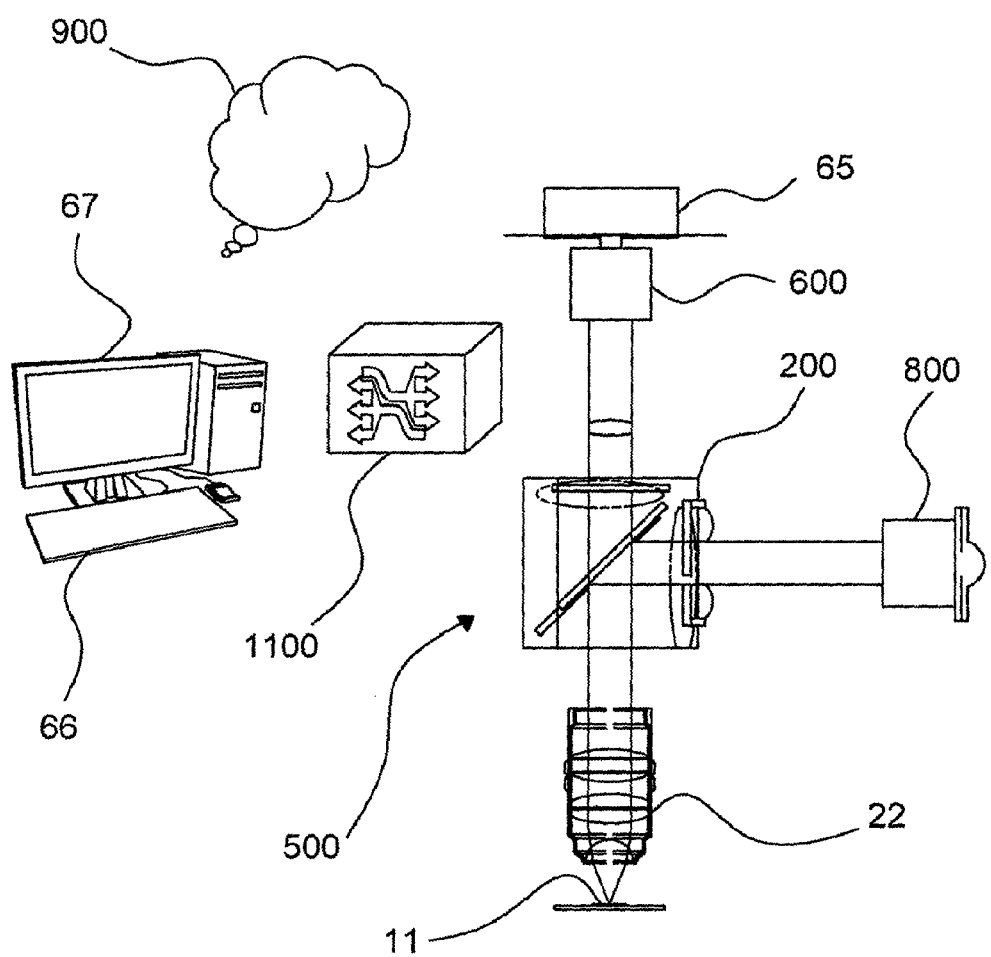

The preferred implementation of the method according to one embodiment of the invention is a hardware platform and algorithms, referred to as the SRCDP platform, 500, shown in FIG. 5.

The SRCDP platform, 500, implements the method according to an embodiment of the invention, by combining the two PSIT and PDOS methods above.

In one of the embodiments, the platform SRCDP observes, FIG. 5, a biological sample, 11, including a plurality of nano emitters. The result of the observation of the biological sample by the SRCDP platform is the acquisition of superresolution information, representative of the observed sample.

Figure 8:
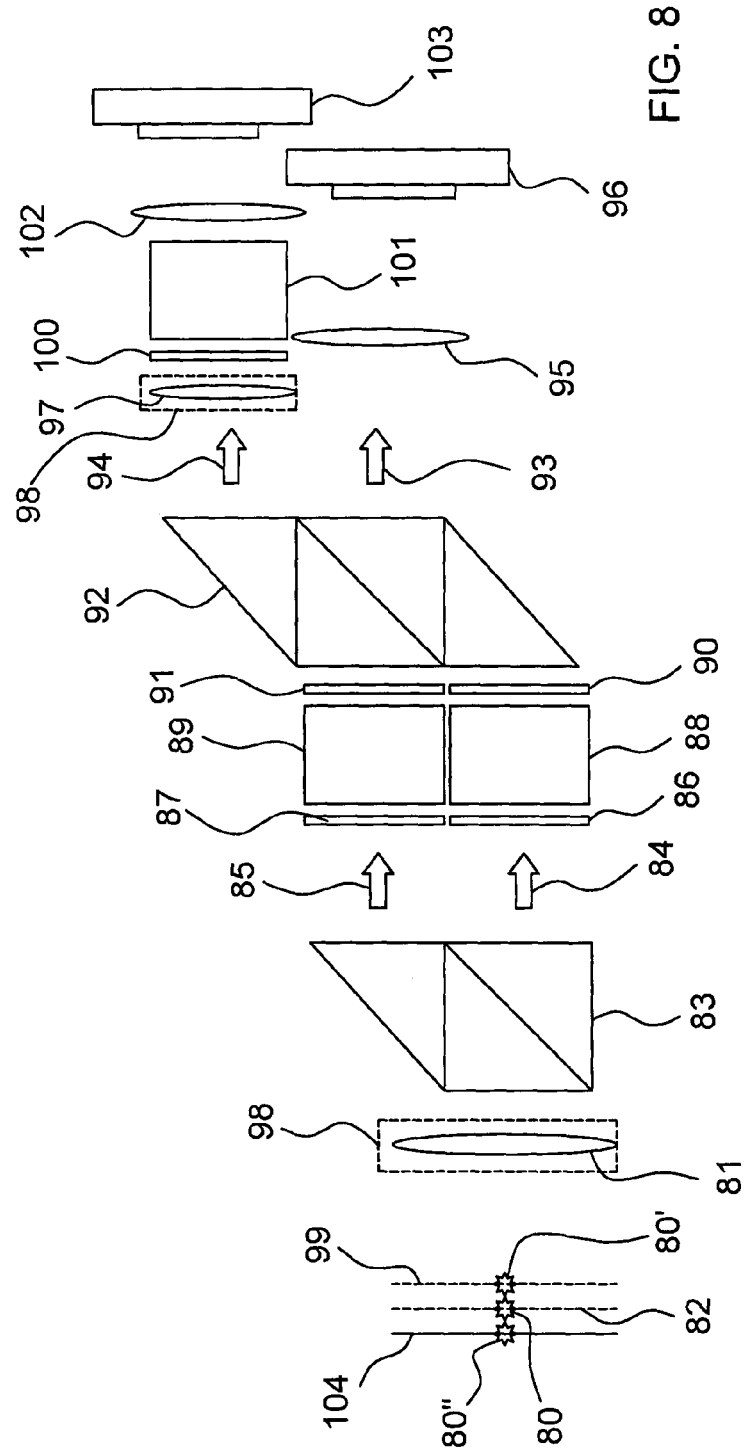
Figure 9:
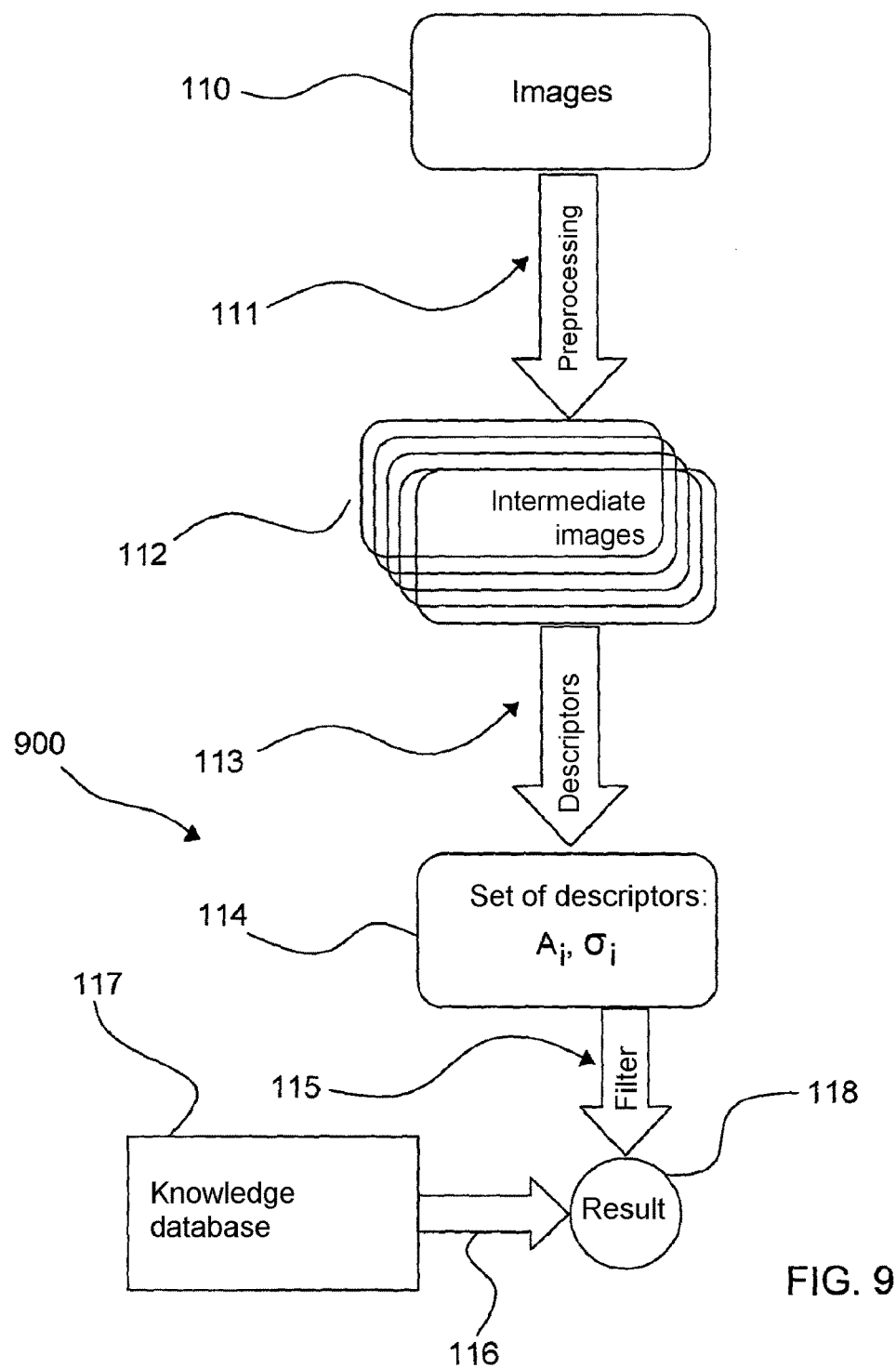

The platform SRCDP, 500, FIG. 5 includes mainly:

In its hardware part:

A confocal microscope 200, adapted or optimised, similar to the confocal microscope, described previously, and including all appropriate components, as previously described Two new and complementary optical modules, mounted on a standard microscope. The two new optical modules are optical modules LatSRCS, 700, and LongSRCS, 800, described in detail later with reference to FIGS. 6 and 8, respectively. The optical module 700 LatSRCS, implements the steps of illumination required for implementing the PSIT method according to one embodiment of the invention. The optical module LongSRCS, 800, implements the steps of the light intensity distribution in a plurality of emerging Images of the PDOS method according to an embodiment of the invention and;

Module algorithmic SRCDA, 600, which will be described by referring to FIG. 8, is able, to reconstruct superresolution information of the biological sample from images created by the platform SRCDP.

Figure 6:
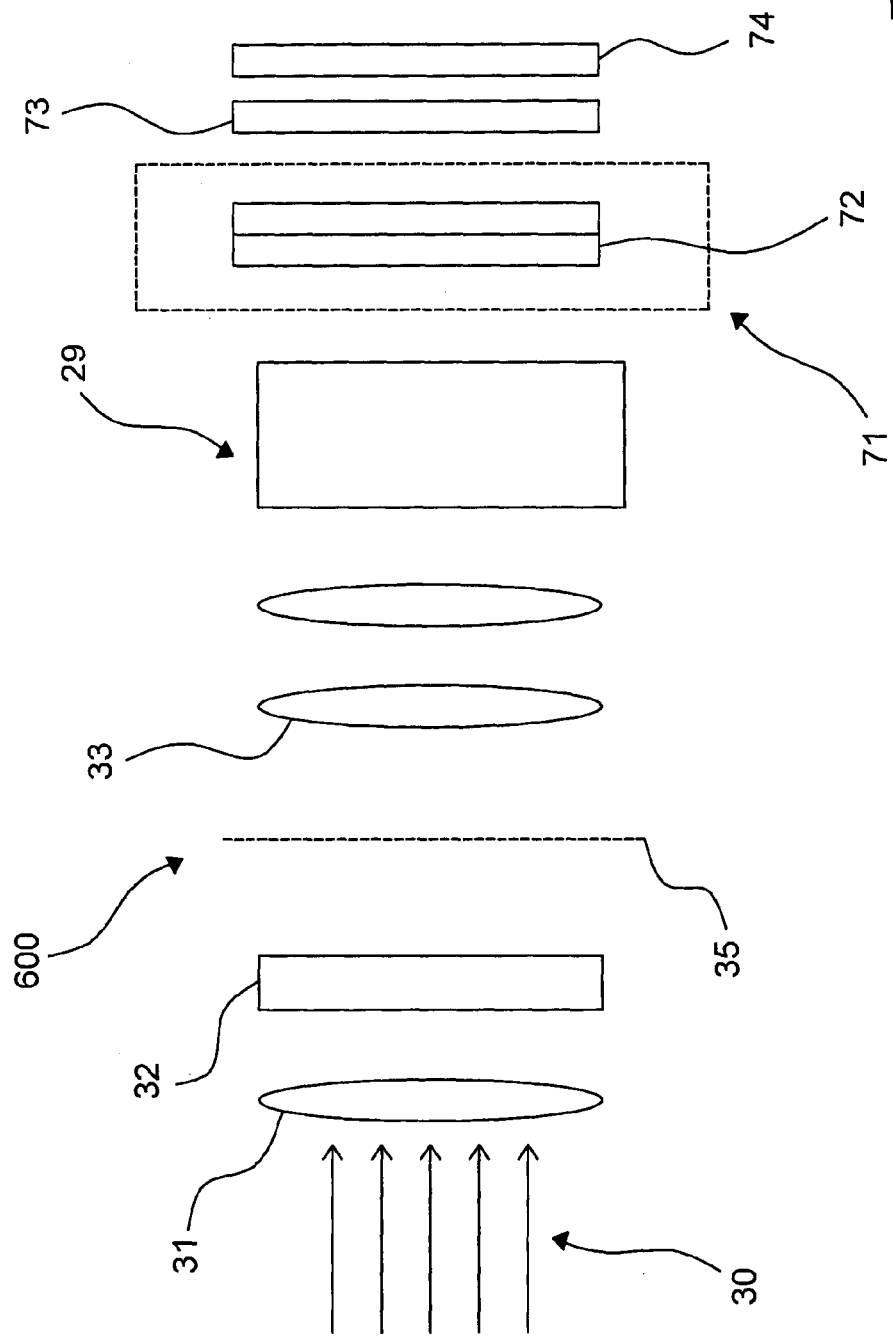

Other auxiliary elements, such as computer 66 and software 67, necessary for the realization of the platform, LatSRCS Optical Module Implementing the PSIT Method We describe, with reference to FIG. 6, an optical module according to an embodiment of the invention, the optical module LatSRCS, 700, and its specific function in microscopy.

The optical module LatSRCS, 700 according to this embodiment is an optical module, projecting on a plurality of nanoemitters in a sample, a sequence of compact light distributions of different topology. Each nanoemitter fluoresces with a sequence of fluorescent light intensities dependent on the incident intensity on the nanoemitter and characterizing the lateral position of the nanoemitter. In most embodiments, the light compact distributions of different topologies are created by interference with variable amplitudes and phases between an ordinary wave and singular wave. In the preferred embodiment, the regular and singular waves are created by a thin conical crystal.

The optical module LatSRCS, 700, is positioned in the illumination path of the confocal microscope 200; it projects a sequence of compact light distributions of different topologies on the sample 11 using the confocal microscope objective 200. In the preferred embodiment using the conical diffraction, the incident intensity at a specific position on the sample 11 will be proportional for each light distribution pattern, to a specific combination of the Stokes parameters.

The optical module LatSRCS, 700, uses an inherent feature described above, specific to the nanoemitter, which samples the intensity of light incident on its precise position (the nanoemitter), and reemits fluorescent light dependent on the incident light. It is remarkable that the measured information is directly related to the position of the nanoemitter in the compact light distribution. This information is frozen by the functionality of the fluorophore, its ability to absorb and re-emit light, breaking the optical chain. This information is carried by the fluorescent light as an emerging light distribution recoverable by a detector assembly 65.

If the incident light varies temporally according to a sequence of compact light distributions of different topologies, the intensity of the fluorescent light reemitted varies in the same proportions. The sequence of the re-emitted fluorescent light is proportional to the sequence of compact light distributions of different topologies. From this information, it is possible to retrieve the position of the nanoemitter, as explained below.

The PSIT method, according to embodiments of the invention, refers to the projection of a sequence of compact light distributions of different topologies in a microscope, the interaction with the parsimonious object and the continuous object, collecting the reflected light by the objective of microscope, 22, detecting the fluorescent light or not, by the improved detector assembly 65, and the analysis of the information by a suitable algorithm. In some embodiments, the improved detection assembly, 65, comprises a single detector, and recovers only the overall intensity as a function of time, while in other embodiments the improved detection assembly includes a small area of pixels and recovers also the spatial distribution of the fluorescent light. All retrieved information consisting of a plurality of images, the named as lateral superresolution images.

In one of the embodiments, the contribution of a nanoemitter in the illuminated volume positioned in a specific lateral superresolution image is proportional to a specific combination of the Stokes parameters of the incident light at the nanoemitter position.

Lateral superresolution images, the information created by compact light distributions of different topologies, is new and was not present in the prior art. This new information helps to refine the position of the nanoemitters or the spatial distribution of the continuous object, to quantify the number of nanoemitters present in the illuminated volume and to differentiate multiple nanoemitters present in the same volume.

We refer now to FIG. 6, which is a simplified schematic illustration of an optical module LatSRCS, 700 in accordance with an embodiment of the present invention.

FIG. 6 shows an optical module LatSRCS, 700; it includes all the components of the module of conical diffraction, of FIG. 3, which are implemented in the same way as in the module 300 of conical diffraction. The optics of the light source of the scanning confocal microscope is assumed to be achromatic and infinite conjugate, although other conditions can be adapted using auxiliary optics. The incident light entering from the light source is parallel, 30. The optical module itself, 700, comprises a first lens 31, an achromatic 32, or a subset achromatically performing the functionality of a conical crystal as explained previously, and a second lens 33; a partial polariser, 29, described above, may also be added. The first two lenses 31 and 33 are preferably configured in the form of a Kepler telescope of ratio of 1:1; the conical imaging plane, 35, is placed in the common focal plane of the lenses 31 and 33. The numerical aperture of the first lens, 31, determines the parameters of the conical diffraction effect through the conical normalized radius, defined below. The second objective 33, restores the parallelism of the light, to inject it in the microscope. It further comprises a sub-module of polarization control 71, including, for example, a rotating quarter-wave plate, a pair of liquid crystal light valves or a Pockels cell, 72 and an analyser 73. The information of the Stokes parameters can be converted into sequence information, through a sequence of light distributions spatially differentiated and carrying sequential information, as described above.

Figure 7A:
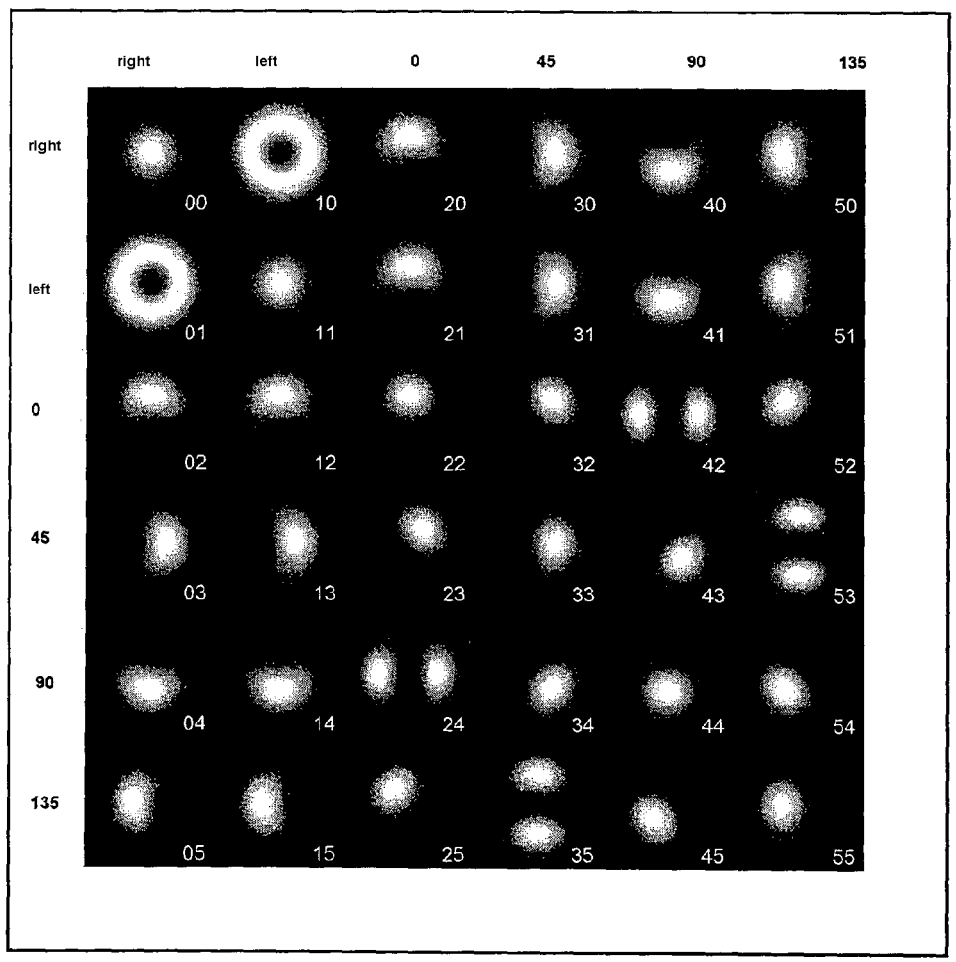

Referring to FIG. 7a, this figure shows the light distribution, created through a conical crystal with a normalized conical parameter $\rho_0$ of 0.388, calculated by a scalar approximation for different input and output polarization states, including at inlet or outlet either a circular or linear polariser or a radial or azimuthal polariser. These light distributions were calculated in an imaging intermediate plane and not at the focus of the objective to separate the conical refraction from vectorial effects. The—input and output—states of polarization are characterized by their angle for linear polarizations and their chirality for circular polarizations.

Figure 7B:
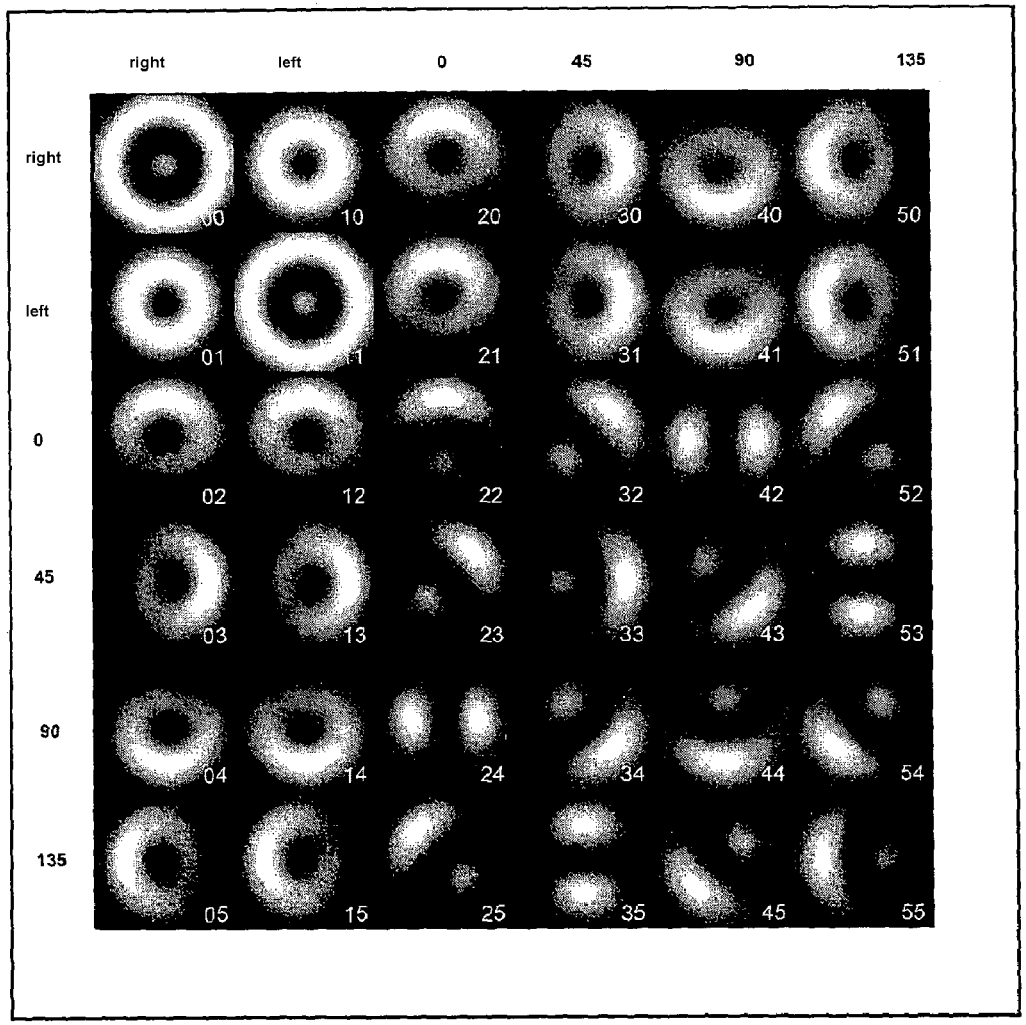

Referring to FIG. 7b, this figure shows the light distribution, created through a conical crystal with a normalized conical parameter $\rho_0$ of 0.818, calculated by a scalar approximation for different input and output polarization states, including at inlet or outlet either a circular or linear polariser or a radial or azimuthal polariser. These light distributions were calculated using the software Diffract from MMresearch Company.

These light distributions were calculated in an imaging intermediate plane and not at the focus of the objective to separate the conical refraction [should be diffraction] effects from vectorial effects. The—input and output—states of polarization are characterized by their angle for linear polarizations and their chirality for circular polarizations.

These tables present a large number of different transfer functions, including the case including at inlet or outlet circular, linear, azimuthal or radial polarisers. This description has to be completed by including circular, linear, azimuthal or radial polarisers described in the figures, the case of elliptical, dichroic or partially dichroic polarisers, and polarisers varying spatially. Also, as illustrated in FIGS. 7a and 7b, these transfer functions vary considerably as a function of the standardised conical parameter $\rho_0$. Also, the introduction of two conical crystals, or one conical crystal and one uniaxial or biaxial crystal (in which light propagates in one direction of propagation different to that of conical diffraction) in cascade allows an even greater number of transfer functions as illustrated for two conical crystals in FIG. 7c.

In summary, in this patent application we reference under the term of conical diffraction transfer function the set of transfer functions which can be obtained by means of a low (<6) number of crystals in cascade, and polarization elements, static or dynamic, uniform or varying spatially.

We denote mainly the following light distributions:

The fundamental, FIG. $7a_{00}$ and FIG. $7a_{11}$ obtained between parallel circular polarisers, which is a distribution close to the Airy distribution The vortex: FIG. $7a_{01}$ and FIG. $7a_{10}$ obtained between crossed circular polarisers The distribution that we called the "crescent moon" distribution; the subfigures $7a_{0,2-5}$, $7a_{1,2-5}$, $7a_{2-5,0}$ and $7a_{2-5,1}$, are obtained between a circular polariser and a linear polariser with a variable angle. This distribution is antisymmetric and the axis rotates following the linear polariser axis.

The distribution that we called the "half-moons" distribution; the subfigures FIGS. $7a_{42}$, $7a_{35}$, $7a_{24}$ and $7a_{53}$ are obtained between two crossed polarisers; this distribution is symmetric.

The more complex light distributions, FIG. 7b, for a crystal with a normalized conical parameter, $\beta_0$, greater than 0.5

The creation of additional light distributions using two— or more—crystal cascading conical crystals (not shown) with or without static or dynamic polarizing elements between the crystals The different light distributions are carried out by modification of the inlet or outlet polarization. The different light distributions follow the same optical path and the optical system creating these distributions is an optical system of common path, such as defined previously. There is a number of polarization elements having different polarization at different wavelengths. The use of one of these elements creates two waves compact, either regular or singular at two wavelengths or a regular wave at one wavelength and a singular wave at another wavelength. Such a device enables far simpler implementation of emission-depletion concepts limited in some cases by tolerances or by vibrations of the optical system.

Redundancy and Random Phase Variations

The elementary light distributions described in FIG. 7 can be obtained in several ways. In addition, some of them can be obtained as a linear combination of other elementary light distributions, e.g. the vortex can be obtained by the sum of any two orthogonal "half-moons" light distributions.

This redundancy allows some averaging of random phase errors inevitably present in many measurement process of biological objects. This reinforces the robustness of the measurement methodology of the embodiments of the invention and its applicability.

New light distributions can also be obtained as mathematical combinations of elementary light distributions. The "pseudo-vortex", light distribution, calculated from arithmetic combinations of the four distributions "in crescent moon" has the feature of having a strong curve at the origin.

Method PSIT was originally designed to allow lateral superresolution, however PSIT method can also be used to obtain the longitudinal position of a nanoemitter. Indeed, some elementary light distributions are relatively insensitive—within reasonable limits—to a variation of the longitudinal position of the nano emitter, others are rather sensitive. A sequence of compact light distributions, some of them independent and some of them depend on the longitudinal position would reveal the longitudinal position of nano emitters.

In addition for the light distributions which are highly dependent on the longitudinal position of the nanoemitter, a series of elementary light distributions slightly shifted longitudinally, one relative to the other can be projected on the sample, allowing a set of images containing longitudinal information.

In addition, some more complex elementary light distribution, consisting of more complex overlapping of waves with a strong longitudinal dependence exist, e.g. the "three-dimensional dark spot" described by Zhang [26], which create a black spot surrounded in three dimensions by a luminous sphere. These "three dimensional dark spots" consist of a superposition of Laguerre-Gauss functions, which can be achieved within a laser cavity or using a hologram or a phase plate, as suggested by Zhang, or using uniaxial or conical crystals as suggested by the inventor.

All these variants of the measurement methodology are considered part of the invention. The inventor has yet chosen in the preferred implementation to separate in two optical modules, disjoint but complementary, lateral measurement and longitudinal measurement to reduce the complexity of each of the modules.

Vector Effects

The theory developed so far describes the light distribution in the imaging plane of the microscope 35. The distribution of the light projected onto the sample is, according to the theory of the geometrical imaging, a reduced image of the light distribution in the image plane.

However, as described extensively in the literature, for a high numerical aperture objective, the imaging geometric theory is not accurate and vector effects must be taken into account. These effects consist essentially in the presence of a component, longitudinally polarized.

Referring again to FIG. 6, to mitigate vector effects, it may be advantageous to maintain the final analyser fixed and to add an additional element, fixed or variable, the output polarization adaptation submodule, 74, for controlling the output polarization. We found that an output polarization with circular symmetry greatly reduces the effects vector. Such polarization can be circular, radial or azimuthal. For circular polarization, the output polarization adaptation submodule, 74, is simply a quarter wave retardation plate. In this case, the elements of longitudinal polarization have vortex symmetry and integrate harmoniously into the system with only a small change in the form of the Stokes parameters, even for microscope objectives with high numerical aperture.

Alternatively, the output polarization adaptation submodule, 74, may be variable and adapted to the topology and the symmetry of each of the compact light distribution.

LongSRCS Optical Module Implementing the PDOS Method

We describe below an optical module LongSRCS with more details. The system of longitudinal superresolution, according to an embodiment of the invention, channels the incident light intensities of a plurality of point sources located in a small illuminated volume, either on separate detectors or on distinct geometric positions on the same detector or on a combination of both, as function of the spatial position of each point source.

In simpler words, the intensity emitted by a fluorophore positioned longitudinally at the point A will be physically separated from the intensity emitted by a nanoemitter positioned longitudinally to point B.

The optical module LongSRCS, according to an embodiment of the invention, allows the separation in volume slices, different slices of the illuminated volume being physically separated on different sets of detectors.

In the preferred embodiment, which will be explained below, the optical module LongSRCS separates an illuminated volume in at least three adjacent slices, separating the middle slice from of the other two slices on sets of independent improved detectors, and creating a spatial differentiation between the two remaining slices on the same set of improved detectors.

We refer now to FIG. 8, which is a simplified schematic illustration of a LongSRCS optical module, 800, according to an embodiment of the present invention.

The optical module LongSRCS channels the incident light intensity of a plurality of point sources located in a small volume of light, either on separate detectors or on distinct geometric positions on the same detector either a combination of both, depending on the longitudinal position of each point source.

In a preferred embodiment, it operates on the nanoemitters, represented by 80, 80' or 80", according to their longitudinal position. It comprises a first collimating lens 81, which may consists, in some embodiments of the microscope objective 4.

The nanoemitter 80 is positioned in the focal plane of the collimating lens 82, the light from the nanoemitter 80, emerging from the collimating lens 81 is collimated.

The nanoemitters 80' and 80" are placed before and after the focal plane of the collimating lens, 82, at a distance of $\pm\Delta z$, the light from the nanoemitters 80' or 80" emerging from the collimating lens 81 being convergent or divergent.

The LongSRCS optical module includes a polarization beam separator, shown in

FIG. 8, in the form of a lateral displacement polarization beam splitter, 83. The polarization beam splitter splits the incident light, assumed to be non-polarized in two polarization channels, 84 and 85, having orthogonal linear polarizations. The system can be simplified by using a single polarization channel instead of two, if the incoming light is already polarized or at the cost of a loss of half of the intensity of the incident light, for unpolarized light.

Two quarter wave plates, 86 and 87, transform, for each channel, the linearly polarized circular polarizations.

An achromatic conical crystal, or a subset achromatically performing the functionality of a conical crystal as explained previously, is placed in each of the channels 88 and 89. In each channel, a conical diffraction setup, as described in the FIG. 3, is constituted by the collimator lens 81, acting as a primary objective of the setup of conical diffraction, 31, and a conical crystals, 88 and 89. Conical diffraction pattern will be complemented by a second lens 33, in the following.

For the nanoemitter 80, positioned in the focal plane of the collimating lens 82, the light emerging from the collimator lens 81, is, as discussed above, collimated; referring to the setup of conical diffraction, the Numerical Aperture of the collimating lens 81, in the image space, and the normalized radius cone are zero, so that the effect of conical diffraction on the beam from the nanoemitter 80 is zero. Therefore, the conical crystal does not change the geometry of the fluorescent light emitted by the nanoemitter, or its polarization, which remains circular with the same chirality.

For nanoemitters, 80' or 80", which are not positioned in the focal plane of the collimating lens 82, the light diverges or converges; Referring again to setup conical diffraction described above, the Numerical Aperture in the image plane of the collimating lens 81, which is equivalent to the first lens of the conical diffraction setup, 31, is non-zero. For a given value $\Delta z$ defocus, positive or negative, most of the light emerging from the crystal is contained in the conical wave vortex, which has a form of a vortex, and is inverted chirality.

The functionality of the conical diffraction set-ups positioned in each of the channels is to distinguish the collimated light from the light converging or diverging by reversing the chirality of the circular polarization of the light for converging or diverging light.

Two other blades quarter wave plates, 90 and 91 transform the circular polarizations, emerging each channel, linear polarizations. We refer, for each channel, to the linear polarization, which would have emerged from the retardation plate, if the crystal had been removed, as the polarization of collimation The optical module comprises a LongSRCS combiner/separator of four ports, shown in FIG. 8 as a lateral separation four ports combiner/separator 92. For each channel it separates the two polarizations, and merges the two polarizations of collimation in the same path, the path of collimation, 93, and the polarized light orthogonal to the collimation polarization in another path, the path of non-collimation, 94. The directions of the axes of the quarter wave plates, 86, 87, 90 and 91 must be chosen appropriately.

The combined beams do not interfere, because they come from originally unpolarized beam.

The incident light into the path of collimation is focused onto the detector of collimation, 96, using the focusing lens of the collimating path, 95, which behave functionally as the second lens, 32, of the conical diffraction setup.

In the path of non-collimation, an additional lens 97 is inserted, and the additional lens 97, together with the collimating lens, 81, creates a new lens system, 98, whose focal plane, 99 is positioned at a different position of the focal plane of the collimating lens 82, the position of the nanoemitter 80'. An additional quarter wave plate, 100, cancels the action of the quarter wave plates, 90 or 91, turning back the incoming beams of each of the channels of polarization, to the circular polarization, which they were at the output polarized crystals conical, 88 or 89.

An additional conical crystal, 101, is added in the way of non-collimation as a third conical diffraction setup—the auxiliary conical diffraction setup—with the system of lenses 98, acting as the first lens of the conical diffraction setup, 31.

The nanoemitter 80' have been positioned before the focal plane of the collimating lens, 82, at a distance of $\Delta z$, but, relative to the lens system 98, it is positioned at the focal plane 99. The light from the nanoemitter 80' had already been converted into a vortex by one of the conical diffraction set-ups consisting of the collimating lens 81, and one of the conical crystals 88 or 89, depending on the channel of polarization travelled by the light. The light from the nanoemitter 80' is collimated at the output of the lens system, 98, after the additional lens, 97.

Referring to the new conical diffraction setup, the numerical aperture of the lens system in the image space, and the normalized conical radius are zero for nanoemitter 80'; the effect of conical diffraction, of the auxiliary diffraction setup, on the beam emerging from nanoemitter 80' is zero. Therefore, the conical crystal does not change the geometry of the fluorescent light emitted by the nanoemitter. Light incoming from a nanoemitter 80', is a vortex before and after the conical crystal 98.

The nanoemitter 80" had been placed after the focal plane of the collimating lens, 82, at a distance of $\Delta z$ on the lens system 98; it is placed at a distance of $-2\,\Delta z$ of the focal position, 99, and the light from the nanoemitter 80" converge also to the output of the lens system, 98, after the front lens, 97. The light from the nanoemitter 80", has already been converted into a vortex by one of conical diffraction setup consisting of collimating lens 81, and either one of the conical crystals 88 or 89, depending on the channel of polarization followed by the light. The conical crystal 101 changes the light from nanoemitter 80", and, for relevant parameters of the material, i.e. the size and orientation of the conical crystal, it reverts to a regular wave, slightly different from the Airy disk.

The objective lens of the non-collimation path, 102, is adapted to focus the plane containing nanoemitter 80", which is a regular wave, 104, and not the nanoemitter 80', which is singular on the pixelated detector assembly, 103. The incident light emerging from a fluorophore positioned in plane 104, such as the fluorophore 80", is perfectly focused and is positioned at the centre of the pixelated detector, 103. Incident light emerging from a nanoemitter positioned at the plane 99 is a vortex and therefore focuses on an outer ring with a central zero. By separately recording the intensity at the centre and the intensity at the outer part of the detector, it is possible to separate, with a slight overlap the incident light from planes 104 and 99. In addition, a nanoemitter positioned at the plane 104 as the nanoemitter 80', is slightly delocalised because the objective is calculated so as to focus on the detector plane 104. This improves the action of the optical module LongSRCS, pushing further the intensity of the vortex centre and reducing duplication.

This simplified description of a preferred embodiment of the optical module LongSRCS, 800, allows many possibilities of variations and adaptations by changes in the optical design through changes known to an expert. These changes include, but are not limited to: the crystal material and orientations, the choice of polarization components, the choice of the polarization axes of the cascade elements, the number of sensors, or, reversing the roles of nanoemitters 80' and 80". In addition, the module is ideally conditioned to be constructed as a set of monolithic subsets or even as a single monolithic unit.

PDOS Method and Lateral Measurements

Method PDOS was originally designed to allow longitudinal superresolution, however PDOS method can also be used for measuring the lateral position of a nanoemitter. Indeed, the elementary light distributions are also sensitive to variation of the lateral position of the nanoemitter. For a plane sample, in the case where the light projection is not possible, the method PDOS may replace the method PSIT for performing superresolution measurements.

All these variants of the measurement methodology are considered part of the invention. The inventor has yet chosen in the preferred implementation to separate into two disjoint, separated, but complementary optical modules the lateral measures from the longitudinal measures to reduce the complexity of each one of the add-ons.

Detection Module

The corollary of the potency of the measurement methodology is the requirement of a more complex detection module, able to detect and retrieve information created. In scanning confocal microscopy, the detector is a detector consisting of a single element as a PMT or SPAD. The acquisition time of the detector is determined by the scanning mechanism.

The measurement methodology requires, in some embodiments, two—or more—detector modules, instead of one, in the case of two modules, the fundamental and vortex detector modules. In addition, the measurement methodology requires, in some embodiments, for each illuminated volume, the acquisition of the optical information on a small spatial grid, typically 16*16, at a rate higher than the pixel time, due to the need to identify and quantify the sequential signals.

An improved detection module, 65, may be implemented using small detectors with low number of pixels. Such a module would not have been possible ten or twenty years ago, due to the lack of appropriate technologies. Today, small detectors with small number of pixels, at high speed, with low noise characteristics are available on the basis of several technologies. SPAD arrays with a small number of pixels, such as 32*32 have been shown recently with acquisition rates up to 1 MHz. The improved detector module 65, may also be implemented using CCD, EMCCD or CMOS sensors. CCD sensors, CMOS and EMCCD with a small number of pixels exist or can be specifically designed.

In addition, CCD sensors, CMOS EMCCD can be used using features as region of interest, sub-windowing or "binning", "crop" or "fast kinetics" modes, available for some detectors.

The spatio-temporal information referenced herein is the position and the time of the impact of each fluorescent photon. In real systems, the spatio-temporal information is corrupted by the noise of the detector, which creates incorrect photons, and by inefficient detection, creating photons which are not detected, thereby reducing performance. In SPAD arrays, for each photon, the pixel that has detected it and the time of impact are received, i.e. the full spatiotemporal information is available. For CCD sensors, CMOS or EMCCD, the acquisition of multiple frames is necessary to approximate the spatio-temporal information.

In several implementations we will refer to separate detectors; in many cases the sensor can be either physically separated or consisting of different areas on a single detector, or a combination of the two previous cases.

Algorithms SRCDA

The reconstruction algorithm detailed above applies not only in the case of a given field analysed by means of PSIT and PDOS methods, but also in the case of a field of larger dimension analysed by scanning. In the case of scanning, the direct model is enriched by the fact that coverage between the different positions of signals projected takes into account, at a given point, more measurements. But considering offset projected signals brings no additional complexity to the resolution methodology plane, since these offset signals only add to the list of projected signals.

Algorithm of the Compound Optical Process Implementing Measurement Methodology

The compound optical process according to at least one embodiment of the invention is the logical complement of the SRCDA algorithm. Indeed, the reconstruction obtained by the SRCDA algorithm can lead to the conclusion that an additional image would improve performance of the measurement. The SRCDP microscopy platform allows the acquisition of one—or more additional images from a set of light distribution of the PSIT or PDOS methods.

An example is explained below.

Position Measuring Point by the Method PSIT

PSIT method can be used as a technique for measuring the position of a nanoemitter with high precision.

Consider a nanoemitter positioned at the position x, y in Cartesian coordinates and $\rho$, $\theta$ in polar coordinates. A sequence of illumination consisting of a fundamental wave, and a couple of the so-called "half-moon" distributions aligned along orthogonal axes is projected onto the nanoemitter.

The pre-processing procedure created two images:

A "top hat" image consisting of the sum of the three images of the sequence and a vortex image consisting of the sum of the two images half-moons.

A first descriptor is the Cartesian position is calculated using the algorithm of the centroid of the image "top hat".

Figure 10:
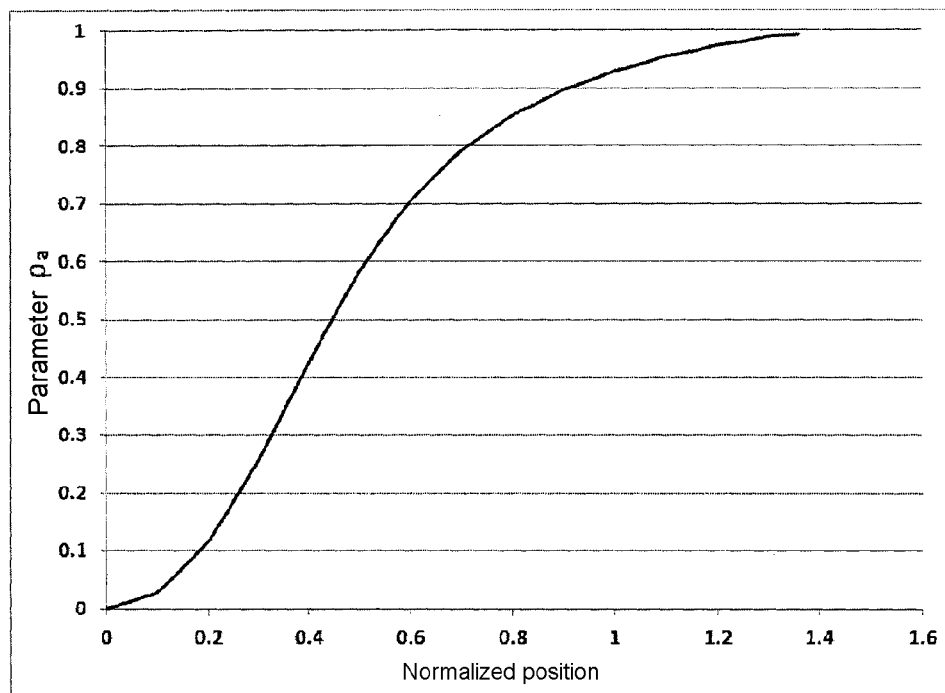

Referring to FIG. 10, the radial position p can be measured unambiguously by measuring a parameter, $\rho_a$, equal to the arctangent, of the intensity ratio between the normalized intensity emitted by illuminated by the nanoemitter wave vortex, $I_V$, and the normalized intensity emitted by the nanoemitter illuminated by the fundamental wave, $I_F$, normalized by a factor $\pi$. In fact:

the normalized intensity emitted by the nanoemitter illuminated by the fundamental wave varies from 1, at the centre of the fundamental wave, to 0, at radius of Airy, the normalized intensity, emitted by the nanoemitter illuminated by the vortex wave varies from 0 for the centre of the vortex to 1 at the vortex maximum and reach 0 to a value slightly higher than the radius of Airy. The arc tangent of the ratio is a monotonic function.

The azimuth position can be measured by measuring the intensity ratio between the total intensity emitted by the nanoemitter illuminated by the first half-moon distribution, $I_H$, and the total intensity emitted by the nanoemitter illuminated by the second half moon distribution, $I_{ve}$. The ratio between these two intensities is a geometric tangent square law:

$$\frac{I_{VE}}{I_H} = \tan^2\theta \qquad (EQ. 10)$$

Both measures are redundant. This redundancy is a measure to qualify the observed object as a single point and separate it from other objects potentially present in the sample.

Direct application of the use of the PSIT method according to an embodiment of the invention for measuring the position of a nanoemitter with high precision is the integration of this measuring technique into a novel technique for local stochastic optical reconstruction. One of the limits of the applicativity of stochastic techniques is the measuring process, needing a large number of images and therefore long measuring time and strong phototoxicity. Use of the PSIT technique according to at least one embodiment of the invention, which measures the position of a light emitter, at a resolution well above the Airy disc, at rates from micro or nanoseconds enables extension of stochastic techniques to many novel applications.

The images resulting from use of the PSIT method can also be processed using the generalised Hough method, for recognising structured objects, line, circle or other, in an image.

Representation in a Higher Dimensional Space: CartesianoPolar Representation

This result can be generalized. We introduce in this paper an entire new representation of a plane, combining the Cartesian representation and the polar representation. We named this representation the CartesianoPolar representation. A point in the plane is represented by a quadruplet: x, y, p, θ. This representation is non-Euclidean and redundant. A similar representation of space can be defined mutatis mutandis.

At first sight this representation seems unnecessary: it is a highly complex representation for a much simpler reality. It is well known that the position of a point in a plane can be represented, alternatively, either by using the Cartesian coordinates, x and y, or either by using polar coordinates p and θ.

Representation in a Higher Dimensional Space: Pythagoras Space

In this paper only the simplified version of the CartesianoPolar representation is detailed, wherein a point with coordinates x, y and p is represented. We named this space the space of Pythagoras.

Defining the geometric area to be a two-dimensional surface in three-dimensional space, which fills the constitutive geometric equation $\rho^2 = x^2 + y^2$; assumes a measurement system that simultaneously measures x, y and ρ, as the measurement system such as described in the previous paragraph together with a centroid algorithm on the same data. A point will be physically positioned in the space of Pythagoras, on the geometrical surface. Consider the case of two or more physical points: The centre of gravity of the two points of measurement is, in general, outside the geometric surface and creates a point outside this area. This representation is a mathematical formalization and generalization of the deterministic algorithm for separating the case of an isolated point from that of an aggregate of points previously described.

Recognition and Measurement of Two Points: A New Resolution Criterion

Consider now two nanoemitters of the same intensity positioned symmetrically about the centre at positions, ρ, θ and ρ, −θ in polar coordinates. We will use the system described in the previous paragraphs. Three descriptors give the following results:

The centroid measure the centroid of the light distribution, which will be the origin, The identifier ρ, measure the value of the common radial value of the two nanoemitters, The θ descriptor, which in the case of half-moons contains a degeneracy between θ and −θ, will measure the value θ.

As mentioned above, if the value of the descriptor ρ is not zero, we know that the case study is not a point but two or more. In addition, descriptors ρ and θ allow us to measure the characteristics of the two points at a much higher resolution than that defined by the Rayleigh criterion. Moreover, using a compound process it is possible to separate this case from the vast majority of cases of three or more points. An additional light distribution can be projected onto the sample, a half-moon inclined at an angle θ; the assumption of the presence of two points will be confirmed or refuted based on the results of this image. Indeed, the measured energy will be zero for two points, for a line or for a series of dots aligned in the direction of the angle θ.

Measuring is not limited a priori. Of course, there is at first a practical resolution limit, linked to the quality of the signal, fluctuations and various imperfections. If practical limits are neglected, the resolution limit is associated with the number of photons detected.

Control Module

With reference to FIG. 11 and FIG. 5, in one preferred embodiment of this invention, the various control elements integrated into the platform SRCDP, 500 will be described:

The control module, 1100, using the procedure of systemic control, 1101, monitors and modifies the optical parameters of the platform SRCDP, 500, the electronic parameters of the improved detection module, 65, and the mathematical parameters of algorithmic procedures SRCDA, 900, to optimise the emerging information in accordance with criteria defined by the system or by the user. Control is achieved by varying control systems 1102, 1103 and 1104, of the various elements of the platform, 600, 800 and 900. The control system 1100, also use, if available, external information, 1105, relayed by computer support. Remark: 1105 is not present in FIG. 11.

It is understood that the invention is not limited in its application to the details specified in the description contained here or illustrated in the drawings. The invention is capable of other embodiments and being practised and carried out in various ways. Those skilled in the art will easily understand that various modifications and changes can be applied to the embodiments of the invention such as described previously without departing from the scope of this invention.

Alternative Implementations of the Measurement Methodology

The embodiments of the invention described can be integrated on a fluorescence confocal microscope. Super-resolution system according to embodiments of the invention is a new method of measurement, in addition to or in replacement of existing methods of microscopy. However, the superresolution system according to embodiments of the invention may equally be integrated on other microscopy platforms. These microscopy platforms, as described as examples, include but are not limited to: wide field microscopes, dark field microscopes, polarization microscopes, phase difference microscopes, differential interference contrast microscopes, stereo microscopes, Raman microscopes, microscopes dedicated to a specific task, such as live cell imaging, cell sorting, cell motility or any other instrument optical microscopy as described for example in the reference {Nikon., 2011 #1290}.

In another embodiment of the invention, called a multi-modality mode, the microscope platform also comprises at least one of the following additional modules:
- at least one additional module of different Microscopy modality such as:
- a superresolution module as per another modality,
- a measuring module of molecular mobility and interaction of molecules marked by fluorescence,
- an analysis module of interaction molecular in the cells.

In another embodiment of the invention derived from the multi-modality mode, the Microscopy platform is configured to integrate a confocal mode and/or a "Full field" mode. Such an embodiment can comprise, in addition to the common components of the Microscope, some of the same optical components, detection or algorithmic tools used by the Platform described for embodiments of the invention described.

In another embodiment of the invention derived from the multi-modality mode, the Microscopy platform is configured to integrate Polarization measurement, either polarization anisotropy, or measuring of Jones or Stokes parameters. Such an embodiment can comprise, in addition to common components of the Microscope, some of the same optical components, detection or algorithmic tools used by the Platform described for embodiments of the invention.

In another embodiment of the invention derived from the multi-modality mode, the Microscopy platform is configured to integrate either a localisation Microscopy system or a system of emission depletion using emission stimulated to eliminate fluorescence in the outer regions of the optical excitation impulse response. Such an embodiment can comprise, in addition to common components of the Microscope, some of the same optical components, detection or algorithmic tools used by the Platform described for embodiments of the invention.

A Microscopy platform according to at least one embodiment of the invention can be used in a medical application, for example but without being limited, for ophthalmologic observation. Such use can comprise measuring biological or medical objects of micronic resolution, the resolution being between 1 and 10 µm, for example.

A Microscopy platform according to at least one embodiment of the invention can be used in a medical application, for example but without being limited, for gastric or gastroenterological observation, or for observation of the colon and urinary tracts. In these embodiments information can be acquired via fibre optics, for example.

In another embodiment of the invention the platform is dedicated to measuring low-fluorescence phenomena, such as, though not limited to, autofluorescence.

In a particular embodiment of the method PSIT, according to at least one embodiment of the invention, regular and singular waves are created by conical diffraction, the propagation of an incident regular wave through a biaxial crystal, aligned in the direction of the optical axis, 32.

In another embodiment of the method PSIT, according to at least one embodiment of the invention, regular and singular waves are created by the propagation of an incident regular wave through a uniaxial crystal, replacing the biaxial crystal, aligned in the direction of the optical axis, 32, of the preferred embodiment.

In another embodiment of the method PSIT, according to at least one embodiment of the invention, regular and singular waves are created by the positioning at the Fourier plane of an optical system of a phase plate—such as a spiral phase plate—or a sub wavelength grating, or by positioning a suitable holographic optical element.

In an embodiment of the PSIT method derived from the above the phase or polarization element is dynamic and controllable, such as example a matrix of elements of liquid crystals, or of Pockels, Faraday or Kerr effects. The matrix can be pixelated, either in the form of separate regions or monolithic segments.

In an embodiment of the PSIT method according to at least one embodiment of the invention, interaction between the modes is created, statically or dynamically, interaction in a photonic fibre.

In an embodiment of the PSIT method according to at least one embodiment of the invention, the transmission of "at least two compact light distributions of different topological families" is achieved by fibre optics, including, though not limited to, a photonic fibre.

In another embodiment of the PSIT method according to at least one embodiment of the invention, thick point, not shown, the illumination of the sample comprises a sequence of at least two compact compound light distributions, every compact compound light distribution being composed consisting itself of at least two simple compact light distributions projected simultaneously. Said at least two simple compact light distribution being optically coherent, partially coherent or incoherent relative to each other, said at least two simple compact light distributions being positioned at different spatial positions and said at least two simple compact light distributions differing in at least one of characteristics, such as their central lateral position, their central longitudinal position, their polarization, amplitude or phase. The set of simple compact light distributions contains compact light distributions from different topological families.

In another embodiment of the PSIT method, not shown, compact light distributions are created by different modes of a multimode laser, and the sequence of compact light distributions is created by successively creating modes or, alternatively, by controlling the balance of energy between the modes.

In another embodiment of the PSIT method, not shown, the relationship between regular and singular wave is dynamically changed.

In another embodiment of the PSIT method, not shown, the regular wave and the singular wave are created by a physical separation of the incident beam—in at least—two paths, the transformation in one path, of the regular beam to singular being realized by known means such as phase plates or spiral phase plates, holographic optical element, sub wavelength gratings, uniaxial or biaxial crystals or combination thereof, and the recombination of the two beams using a beam combiner into a single beam. In this embodiment, the differentiation of the compact light distributions can be performed either on the combined beam or on each beam, independently after separation and before recombination.

In another embodiment of the method PSIT, dynamic following, not shown, the system comprises means, including but not limited to controllable mirrors, electro-optical or acousto-optical devices or piezoelectric actuators capable to move the compact light distribution or the sequence of compact light distributions in space with high precision. In the system of dynamic monitoring, the position of the compact light distribution and of the sequence is dynamically controlled so as to follow at least one specific target.

In another embodiment of the method PSIT, black fluorophore, not shown, the compact light distribution or a mathematical combination of compact light distributions is configured so that there is zero intensity at the centre of the compact light distribution.

The system comprises means adapted to move through space the compact light distribution and these means are used to follow the fluorophore and for positioning the fluorophore at its centre, a function of time. When the fluorophore is positioned at the centre of the compact light distribution, without movement, its position can be measured with high accuracy without fluorescent light emerging from a fluorophore, thereby substantially reducing the effects of photo-bleaching. A movement of the fluorophore can be compensated by appropriate movement of the position of the compact light distribution to follow the fluorophore using a small amount of emitted fluorescent light.

In another embodiment of the PSIT method, the position of nanoemitters is obtained with good precision by using light distributions selected such that luminosity at the position of the emitter is minimal but produces significant information. This other embodiment is specifically adapted to low-emitting emitters—capable of delivering only a low total number of photons—such as, though not limited to, autofluorescence effects.

In another embodiment of the method PSIT, dynamic sequences choice, not shown, the system dynamically determines, on the basis of a positioning hypothesis or of a first set of measures, the optimal sequence of compact light distributions.

In another embodiment of the method PSIT, sequences choice and dynamic positioning of the compact light distribution, not shown, the system comprises means, including but not limited to controllable mirrors, electro-optic and acousto-optic devices or piezoelectric actuators, capable of moving in space the compact light distribution, or a combination of compact light distributions with great precision. The system dynamically determines, on the basis of a positioning hypothesis or of a first set of measures, the optimal sequence and the position of the compact light distributions.

In another embodiment of the PSIT method, PSIT method of triangulation, two or more measurement process of the method PSIT, previously described, are carried out on the same sample with different projection axes. The variation in lateral position between the two measurements permits the measurement of the longitudinal position of light nano emitters.

In another embodiment of the PSIT method, the parallel PSIT method, light is incident on a micro lens array—or other optical means, known to experts, allowing the realization of a set of light distributions in parallel, these light distributions being modified by an optical module to perform simultaneously the PSIT method on a large number of discrete points.

In another embodiment of the PSIT method the multispectral PSIT method (not shown), the sample is illuminated sequentially or simultaneously by at least two illumination sequences, each sequence projecting light onto the sample at different wavelengths.

In another embodiment of the PSIT method, an additional polarizing element, fixed or variable, is positioned after the analyser to control polarization of the distributions of projected lights onto the sample, to either limit vectorial effects or create polarization diversity, or measure polarization parameters of the components of the sample.

In another embodiment of the PSIT method, the resulting images are processed using the generalised Hough method, for recognising characteristics in an image.

In another embodiment of the PSIT method, a blinking effect is used to temporally separate light sources positioned at short distances from each other; the blinking effect can be either natural, or caused for example by means of an additional wave, regular or singular, by a photoactivation or photodepletion effect. In this embodiment, which acquires information at very high speed, the point localisation process emitting sequentially utilises the localisation process of a point relative to intensity reemitted as a function of distributions projected, described previously.

In another embodiment of the PSIT method, waves are projected simultaneously and interact in non-linear manner, by multiphoton fluorescence effect (including dual-photon fluorescence) or by Raman effect.

In another embodiment of the PSIT method, light distributions are created by an optical system of common path and injected into a fibre, such that at the outlet of the fibre the compact light distributions of different topological families described previously are produced, this configuration enabling the optical system to create light distributions of the microscope, simplifying the design and use of the microscope. In this embodiment of the PSIT method, fibre can be used in transmission to transmit the different optical modes, created previously, potentially with attenuation which can vary as a function of modes. In this embodiment of the PSIT method the fibre can also create interaction between the modes and the modes emerging from the fibre can differ from those incident in the fibre, given that the system has been designed to take into account and use static or dynamic coupling in the fibre.

In another embodiment of the PSIT method, spectral dependence on the emission of a fluorophore is also modified by a Forster energy transfer effect or by an equivalent effect.

In another embodiment of the PSIT method, the projection of light distributions of different topologies is carried out by conical diffraction and the system has been modified to make it achromatic by the addition of extra elements, such as dispersing elements known to those skilled in the art, such as prisms and networks, or by modification of internal elements such as lenses or the use of two or more crystals having inverse dispersions.

In another embodiment of the PSIT method, the projection of light distributions of different topologies is carried out by conical diffraction and the system has been modified to make it achromatic by the addition of extra elements, such as dispersing elements known to those skilled in the art, such as prisms and networks, or by modification of internal elements such as lenses or the use of two or more crystals having inverse dispersions.

In another embodiment of the PSIT method, the projection of light distributions of different topologies is carried out by conical diffraction and the system has been modified to make it athermal by the addition of extra elements, such as optical elements dependent on temperature known to those skilled in the art, or by modification of internal elements such as lenses or the use of two or more crystals having inverse thermal dependence.

In another embodiment of this invention, the singular wave, originating from an optical system of common path, potentially at a different wavelength to the regular wave, creates a depletion effect of the regular wave by either dropout of fluorophores or by transition between excited states different to the fluorophore. This embodiment differs from the original description by Hell and Wichmann, {Hell, 1994 #1288}, by use of an optical system of common path, considerably simplifying the complexity and alignments of the system, improving its robustness and reducing its cost.

In an embodiment of this invention derived from the previous one, the singular wave, originating from an optical system of common path using conical diffraction or uniaxial crystals, potentially at a different wavelength to the regular wave, creates a depletion effect of the regular wave by either dropout of fluorophores or by transition between excited states different to the fluorophore.

In an embodiment of this invention derived from the preceding one, the optical system of common path uses either conical diffraction or uniaxial crystals, and the regular and singular waves are obtained either by the action of dynamic polarizing elements or by additional an dispersive polarizing element. This embodiment differs from the original description of Hell and Wichmann, {Hell, 1994 #1288}, by use of an optical system of common path, considerably simplifying the complexity and alignments of the system, improving its robustness and reducing its cost.

In another embodiment of the method PDOS, not shown, the channelling of the incoming light from different point sources according to their longitudinal position is realized in the focal plane. It is carried out using an element having polarization properties dependent on the lateral position. Light entering from a point disposed longitudinally relative to a determined plane, will be incident on a given position and will have specific polarization properties, and the incident light from points located at different longitudinal—and lateral—positions, will be incident on other positions in the focal plane, which have different polarization characteristics.

As to a further discussion of the manner of usage and operation of the invention, it should be apparent from the above description. Therefore, any discussion on the form of the use and operation will not be described.

In this respect, before explaining at least one embodiment of the invention in detail, it is understood that the invention is not limited in its application to the details of construction and arrangements of the components set forth in the following description or illustrated in the drawing. The invention is capable of other embodiments and can be practiced and carried out in various ways. In addition, it is understood that the phraseology and terminology employed herein are for the purpose of description and should not be regarded as limiting.

References cited herein teach many principles that are applicable to the present invention. Therefore, the entire contents of these publications are incorporated herein by reference, as appropriate to the teachings of additional or alternative details, features and/or technical information.

Fibre: Transmission

The advantageous use of fibre optics is transmission of the fundamental mode, $TEM_{00}$ mode and only it. However, some configurations of fibre optics, mainly, though not exclusively based on fibres called "Photonic Crystal Fiber" enables transmission simultaneous or not of more complex modes, including vortex modes. It would therefore be possible to deport the optical distributions created by conical refraction by means of fibre optics, enabling major simplification of the optical system.

Also, some fibres "dual-core photonic crystal fibers", {Li, 2012 #1286}, allow interaction between two modes, one of them being a vortex, and provide an additional physical mechanism to create diversified transfer functions.

It is understood that the invention is not limited in its application to the details set forth in the description contained herein or illustrated in the drawings. The invention is capable of other embodiments and of being practiced and carried out in various ways.

Those skilled in the art will readily understand that various modifications and changes can be applied to the embodiments of the invention as described above without departing from its scope as defined in and by the appended claims.

In another embodiment of the SRCDA algorithm, the combinatory SRCDA algorithm, the positions of fluorophores are discretised on a grille (at a certain resolution pitch) and reconstruction is done by systematically scanning all possible positions of at most k fluorophores on the grille (k being considered as a parameter of the method, or else estimated by means of measured intensities, or else estimated by means of a different measurement). For each position k-uplet, the resolution of the inverse problem becomes very simple (estimation of intensities, for example, can be done by a few iterations of the Newtonian method).

In another embodiment of the SRCDA algorithm, the entropic SRCDA algorithm, additional measurements are taken by selecting and sequentially positioning the signals projected at the points which maximise the reconstruction entropy. This dynamic mode therefore optimises the precision of the system relative to the number of measurements.

In another embodiment of the SRCDA algorithm, the obscure SRCDA algorithm, additional measurements are taken by selecting and sequentially positioning the signals projected so as to minimise the quantity of photons absorbed by the fluorophores. This embodiment can be combined with the entropic mode by finding the optimal compromise between collected information and quantity of absorbed photons.

Many superresolution techniques are based on measuring point sources of a size less than a wavelength fraction. The superresolution techniques according to embodiments described enable measuring of point sources, but also of structured objects, for example and mainly segments of lines, circles or even continuous objects. In Biology, this extension will allow measuring of major biological entities such as filaments, neurones and some microtubules.

Even though the descriptions of embodiments, to simplify comprehension of the invention, present applications in Microscopy, more specifically in Biology, and even more specifically in Fluorescence Biology, applications can be extended to general applications of Microscopy and to the whole field of Vision, including artificial Vision.

Embodiments of the invention can be applied, by selecting a different optical system, to many medical applications, for example but without being limited, to ophthalmologic observation. This field of application corresponds to the measuring of biological or medical objects of micronic resolution, the resolution being between 1 and 10 µm.

Also, embodiments of the invention can be applied, as explained later, via fibre optics. This allows many additional applications, for example but without being limited, to gastric or gastroenterological observation, and to observation of the colon and urinary tracts.

It is understood that the invention is not limited in its application to the details stated in the description contained here or illustrated in the diagrams. The invention is capable of other embodiments and being practised and carried out in various ways. Those skilled in the art will easily understand that various modifications and changes can be applied to the embodiments of the invention such as described previously without departing from its field of application, defined in and by the appended claims.

REFERENCES

1. Zeiss, "Zeiss Microscopy and image analysis, http://www.zeiss.com/4125681C00466C26/?Open" (2012).
2. Nikon, "MicroscopyU The source for Microscopy education" (2012), retrieved 6 Mar. 2012.
3. L. Schermelleh, R. Heintzmann, and H. Leonhardt, "A guide to super-resolution fluorescence microscopy" The Journal of cell biology 190, 165-175 (2010).
4. M. V. Berry, "Conical diffraction asymptotics: fine structure of Poggendorff rings and axial spike" Journal Of Optics A-Pure And Applied Optics 6, 289-300 (2004).
5. W. contributors, (\i Wikipedia, The free Encyclopedia\i0\par, 2 Feb. 2012 19:47\par), retrieved {\field{\*\fldinst{HYPERLYNK "http://en.wikipedia.org/w/index.php?title=Super resolution microscopy&oldid=474630789"}} {\fldrslt{\ul\cf1 http://en.wikipedia.org/w/index.php?title=Super resolution microscopy&oldid=4 74630789}}}\f0\fs24\par.
6. Lindegren, "Photoelectric astrometry—A comparison of methods for precise image location," in Modem astrometry; Proceedings of the Colloquium, Vienna, Austria, Sep. 11-14, 1978., 1978), 197-217.
7. J. F. Nye and M. V. Berry, "Dislocations in Wave Trains," Proceedings of the Royal Society of London. Series A, Mathematical and Physical Sciences (1934-1990) 336, 165-190 (1974).
8. S. W. Hell and J. Wichmann, "Breaking the diffraction resolution limit by stimulated emission: stimulated-emission-depletion fluorescence microscopy" Optics letters 19, 780-782 (1994).
9. S. M. Finkbeiner, "Robotic microscopy Systems" (2006).
10. W. R. Hamilton, "Third Supplement to an Essay on the Theory of Systems of Rays" Trans. Royal Irish. Acad., pp 1-144 (1833).
11. H. Llyold, "On the Phenomena presented by Light in its Passage along the Axes of Biaxial Crystals," The London and Edinburgh Philosophical Magazine and Journal of Science ii, 112-120 (1833).
12. M. V. Berry and M. R. Jeffrey, "Conical diffraction: Hamilton's diabolical point at the heart of crystal optics," in Progress in Optics (2007—In Press).
13. M. V. Berry, M. R. Jeffrey, and J. G. Lunney, "Conical diffraction: observations and theory.," Proc. R. Soc. A. 462 1629-1642 (2006).
14. C. Phelan, D. O'Dwyer, Y. Rakovich, J. Donegan, and J. Lunney, "Conical diffraction and Bessel beam formation with a high optical quality biaxial crystal", J. Opt. A, Pure Appl. Opt 7, 685-690 (2009).
15. M. Berry and M. Jeffrey, "Conical diffraction: Hamilton's diabolical point at the heart of crystal optics," Progress in Optics 50, 13 (2007).
16. A. Geivandov, I. Kasianova, E. Kharatiyan, A. Lazarev, P. Lazarev, and S. Palto, "Printable Thin Birefringent Film Retarders for LCD."
17. B. Acharya, A. Primak, T. Dingemans, E. Samulski, and S. Kumar, "The elusive thermotropic biaxial nematic phase in rigid bent-core molecules," Pramana 61, 231-237 (2003).
18. T. Maldonado, "Electro-optic modulators," in Handbook of Optics, M. Bass, ed. (McGraw Hill, Orlando, 1995).
19. J. Kemp, "Piezo-optical birefringence modulators: new use for a long-known effect," Journal of the Optical Society of America 59, 950-953 (1969).
20. D. H. Goldstein and E. Collett, Polarized light (CRC, 2003), Vol. 83.
21. J. B. Pawley, Handbook of biological confocal microscopy (Springer Verlag, 2006).
22. M. Bass, Handbook of optics (McGraw-Hill, 2001).
23. M. Minsky, "Microscopy Apparatus", U.S. Pat. No. 3,013,467 (1961).
24. A. Ferrando, M. Zacares, and M.-Â. Garcia-March, "Voracity Cutoff in Nonlinear Photonic Crystals," Physical Review Letters 95, 043901 (2005).
25. P. Li, J. Zhao, S. Liu, X. Gan, T. Peng, and X. Jiao, "Dynamic behaviors of optical vortices in dual-core photonic crystal fibers," Optics Communications (2012).
26. Y. Zhang, "Generation of three-dimensional dark spots with a perfect light shell with a radially polarized Laguerre-Galsoan beam", Applied optics 49, 6217-6223 (2010).

The invention claimed is:

1. An optical measuring method for determining the spatial or spatiotemporal distribution of a sample, the sample comprising at least one reemitting source, said at least one reemitting source reemitting light as a function of the projected light, according to a determined law, on the sample, the method comprising:
   projecting onto the sample, by means of an achromatic optical projection apparatus, a first compact light distribution;
   detecting light reemitted by said at least one reemitting source and generating a first optical image on a basis of light detected due to the first compact light distribution;
   after generating the first optical image, subsequently projecting onto the sample, by means of the achromatic optical projection apparatus, a second compact light distribution of a different topological family from that of the first compact light distribution, spreading in an optical path identical to that of the first compact light distribution;
   detecting light reemitted by said at least one reemitting source of the sample;
   generating a second optical image on a basis of light detected due to the second compact light distribution; and
   algorithmically analyzing the first and the second optical images to obtain location information of said at least one reemitting source.

2. The optical measuring method according to claim 1, wherein generating a first optical image from detected light is carried out at each instant when the sample is illuminated by the first compact light distribution.

3. The optical measuring method according to claim 1, wherein said first and second compact light distributions of different topological families are created by interference between a regular wave and a singular wave, or between two singular waves, and spatial differentiation between said first and second distributions is created by varying at least one of the following parameters:
   a) at least one of the parameters of the regular wave;
   b) at least one parameter of at least one singular wave and c) phase difference between the regular wave and the singular wave or between the two singular waves.

4. The optical measuring method according to claim 1, wherein the projection of light distributions of different topological families is carried out by conical diffraction in a thin crystal.

5. The method according to claim 1, further comprising transmission along part of the optical path of the compact light distributions of different topological families by fibre optic.

6. The method according to claim 1, further comprising temporal separation by application of a physical effect, by means of an additional, regular or singular wave, by a photoactivation or photodepletion effect, of positioned reemitting sources, in the sample, at minimal distances from each other, using a Microscopy localisation technique.

7. The method according to claim 1, wherein the waves of light distributions projected interact in non-linear manner, by multiphoton fluorescence effect or by Raman effect.

8. The method according to claim 1, wherein said first and second compact light distributions of different topological families are collocated.

* * * * *